United States Patent
Bartlett et al.

(10) Patent No.: US 10,857,271 B2
(45) Date of Patent: Dec. 8, 2020

(54) CLOSED LOOP ELECTRIC BREAST PUMP

(71) Applicant: LANSINOH LABORATORIES, INC., Alexandria, VA (US)

(72) Inventors: Rush Bartlett, Austin, TX (US); Hasan Keser, Izmir (TR); Faik Koklu, Izmir (TR); Koji Matsutori, Alexandria, VA (US); Peter Lawrence Visconti, Gurnee, IL (US); Frank Tinghwa Wang, Taipei (TW)

(73) Assignee: LANSINOH LABORATORIES, INC., Alexandria, VA (US)

( * ) Notice: Subject to any disclaimer, the term of this patent is extended or adjusted under 35 U.S.C. 154(b) by 0 days.

(21) Appl. No.: 16/563,019

(22) Filed: Sep. 6, 2019

(65) Prior Publication Data

US 2020/0078503 A1    Mar. 12, 2020

Related U.S. Application Data

(60) Provisional application No. 62/727,880, filed on Sep. 6, 2018.

(51) Int. Cl.
*A61M 1/06* (2006.01)

(52) U.S. Cl.
CPC ............ *A61M 1/062* (2014.02); *A61M 1/066* (2014.02); *A61M 2205/3306* (2013.01);
(Continued)

(58) Field of Classification Search
CPC ........ A61M 1/06; A61M 1/062; A61M 1/064; A61M 1/066; A61M 1/068; A61M 2205/3327; A61M 2205/3331; A61M 2205/3389; A61M 2205/3379; A61M 2205/3306; A61M 2205/3317;
(Continued)

(56) References Cited

U.S. PATENT DOCUMENTS

| 2,301,781 A | 11/1942 | Higbee |
| 3,911,920 A | 10/1975 | Susinn |

(Continued)

FOREIGN PATENT DOCUMENTS

| EP | 0000339 | 1/1979 |
| EP | 3299043 A1 | 3/2018 |

(Continued)

OTHER PUBLICATIONS

"Elvie Pump" Elvie.com [online]. Retrieved from the Internet: <URL: https://www.elvie.com/shop/elvie-pump>, 12 pages. Retrieved on Sep. 3, 2019.

(Continued)

*Primary Examiner* — Bhisma Mehta
*Assistant Examiner* — James D Ponton
(74) *Attorney, Agent, or Firm* — Merchant & Gould P.C.

(57) ABSTRACT

Examples disclosed herein are relevant to breast pumps. Disclosed examples include breast pumps that automatically adjust various pumping parameters based on data obtained from one or more sensors. The one or more sensors can produce data regarding an amount of milk expressed by a user. The adjusting of the pumping parameters can be configured to, for example, help the user efficiently express milk by utilizing a closed-feedback system that monitors the flow rate of the expressed milk.

18 Claims, 17 Drawing Sheets

(52) U.S. Cl.
CPC ............... *A61M 2205/3317* (2013.01); *A61M 2205/3334* (2013.01); *A61M 2205/3337* (2013.01); *A61M 2205/3344* (2013.01); *A61M 2205/3375* (2013.01); *A61M 2205/3389* (2013.01); *A61M 2205/3393* (2013.01); *A61M 2205/50* (2013.01)

(58) Field of Classification Search
CPC .. A61M 2205/3334; A61M 2205/3337; A61M 2205/3344; A61M 2205/3375; A61M 2205/3393; A61M 2205/50; F04B 43/04; F04B 43/0081; F04B 49/06; F04B 49/065; F04B 51/00; F04B 2203/0201; F04B 2203/0208
See application file for complete search history.

(56) References Cited

U.S. PATENT DOCUMENTS

| | | |
|---|---|---|
| 4,263,912 A | 4/1981 | Adams |
| 4,323,067 A | 4/1982 | Adams |
| 4,673,388 A | 6/1987 | Schlensog et al. |
| 4,799,922 A | 1/1989 | Beer |
| 4,856,663 A | 8/1989 | Epp |
| 4,857,051 A | 8/1989 | Larsson |
| 4,884,013 A | 11/1989 | Jackson |
| 4,930,652 A | 6/1990 | Murphy |
| 4,961,726 A | 10/1990 | Richter |
| 4,964,851 A | 10/1990 | Larsson |
| 4,966,580 A | 10/1990 | Turner |
| 5,531,338 A | 7/1996 | Sklar |
| 5,542,921 A | 8/1996 | Meyers |
| 5,656,026 A * | 8/1997 | Joseph ............... A61F 9/00781 604/9 |
| 5,728,137 A | 3/1998 | Anderson |
| 5,810,772 A | 9/1998 | Niederberger |
| 5,941,847 A | 8/1999 | Huber |
| 5,957,081 A | 9/1999 | Van Der Lely |
| RE36,324 E | 10/1999 | Yoda |
| 6,023,639 A | 2/2000 | Hakky |
| 6,110,140 A | 8/2000 | Silver |
| 6,200,295 B1 | 3/2001 | Burchett |
| 6,461,324 B1 | 10/2002 | Schlensog |
| 6,471,660 B1 | 10/2002 | Covington |
| 6,497,677 B2 | 12/2002 | Silver |
| 6,884,229 B2 | 4/2005 | Renz |
| 6,966,904 B2 | 11/2005 | Ruth |
| 7,029,454 B2 | 4/2006 | Watanabe |
| 7,048,120 B2 | 5/2006 | Pond |
| 7,294,120 B1 * | 11/2007 | Eidsen ............... A61M 3/0258 604/257 |
| 7,320,678 B2 | 1/2008 | Ruth |
| 7,413,557 B2 | 8/2008 | Samson et al. |
| 7,648,467 B2 | 1/2010 | Wang |
| 7,662,127 B2 | 2/2010 | Silver |
| 7,875,000 B2 | 1/2011 | Krebs |
| 8,052,635 B1 | 11/2011 | Kelly |
| 8,360,102 B2 | 1/2013 | Khouri |
| 8,444,596 B2 | 5/2013 | Paterson |
| 8,545,438 B2 | 10/2013 | Kazazoglu |
| 8,961,454 B2 | 2/2015 | Chen |
| 8,979,819 B2 | 3/2015 | Sherman |
| 8,998,879 B2 | 4/2015 | Sherman |
| 9,248,077 B1 | 2/2016 | Kelly |
| 9,539,376 B2 | 1/2017 | Makower |
| 9,539,377 B2 | 1/2017 | Makower |
| 9,616,156 B2 | 4/2017 | Alvarez |
| 9,623,160 B2 | 4/2017 | Alvarez |
| 9,642,952 B1 | 5/2017 | Kelly |
| 9,782,526 B2 | 10/2017 | Sherman |
| D809,646 S | 2/2018 | Mason |
| D811,579 S | 2/2018 | Chang |
| D828,542 S | 9/2018 | Mason |
| 10,080,825 B2 | 9/2018 | Bartlett |
| 10,086,120 B2 | 10/2018 | Bartlett |
| 10,105,474 B2 | 10/2018 | Barral |
| D832,995 S | 11/2018 | Mason |
| D834,177 S | 11/2018 | Chang |
| 10,617,806 B2 | 4/2020 | Bartlett et al. |
| 2002/0072701 A1 | 6/2002 | Nuesch |
| 2002/0156419 A1 | 10/2002 | Silver |
| 2004/0178162 A1 | 9/2004 | Zucker-Franklin |
| 2005/0234400 A1 | 10/2005 | Onuki et al. |
| 2006/0025718 A1 | 2/2006 | Ostrowski |
| 2007/0118078 A1 | 5/2007 | McNally |
| 2007/0235405 A1 | 10/2007 | Fatema |
| 2008/0021380 A1 | 1/2008 | Thommen |
| 2008/0039778 A1 | 2/2008 | Goldie |
| 2008/0177224 A1 * | 7/2008 | Kelly ............... A61M 1/06 604/74 |
| 2008/0255503 A1 | 10/2008 | Quackenbush |
| 2009/0227943 A1 | 9/2009 | Schultz |
| 2009/0254028 A1 | 10/2009 | Brittner |
| 2010/0016789 A1 | 1/2010 | Bosshard |
| 2010/0049122 A1 | 2/2010 | Jaeger-Waldau |
| 2010/0324477 A1 | 12/2010 | Paterson |
| 2011/0054436 A1 | 3/2011 | Griffis |
| 2011/0168292 A1 | 7/2011 | Luzbetak |
| 2011/0251552 A1 | 10/2011 | Brittner |
| 2012/0232524 A1 | 9/2012 | Hyun |
| 2012/0265169 A1 | 10/2012 | Sherman |
| 2013/0005023 A1 | 1/2013 | Min |
| 2013/0030379 A1 | 1/2013 | Ingram |
| 2013/0281983 A1 | 10/2013 | Sherman |
| 2014/0031744 A1 | 1/2014 | Chen |
| 2014/0052106 A1 | 2/2014 | Sherman |
| 2014/0135683 A1 | 5/2014 | Hradisky |
| 2014/0180205 A1 | 6/2014 | Lee |
| 2014/0276629 A1 | 9/2014 | Bauer |
| 2014/0288466 A1 | 9/2014 | Alvarez |
| 2015/0065994 A1 | 3/2015 | Fridman et al. |
| 2015/0133894 A1 | 5/2015 | Sherman |
| 2015/0283311 A1 | 10/2015 | Alvarez |
| 2016/0038662 A1 * | 2/2016 | Felber ............... A61M 1/06 73/861 |
| 2016/0082165 A1 * | 3/2016 | Alvarez ............... A61M 1/062 604/74 |
| 2016/0100888 A1 | 4/2016 | Ferrari |
| 2016/0287767 A1 | 10/2016 | Simmons et al. |
| 2016/0296681 A1 | 10/2016 | Gaskin et al. |
| 2016/0331879 A1 | 11/2016 | Dann |
| 2017/0065753 A1 | 3/2017 | Nowroozi et al. |
| 2017/0072118 A1 * | 3/2017 | Makower ............... A61M 1/062 |
| 2017/0095600 A1 | 4/2017 | Sherman |
| 2017/0182231 A1 | 6/2017 | Aalders et al. |
| 2018/0093024 A1 | 4/2018 | Analytis et al. |
| 2018/0110906 A1 | 4/2018 | Barack |
| 2018/0193559 A1 * | 7/2018 | Hirata ............... A61M 5/1689 |
| 2018/0361040 A1 * | 12/2018 | O'Toole ............... A61M 1/062 |
| 2018/0369464 A1 * | 12/2018 | Aalders ............... A61M 1/06 |
| 2020/0078502 A1 | 3/2020 | Bartlett et al. |

FOREIGN PATENT DOCUMENTS

| | | |
|---|---|---|
| JP | 2003299727 | 10/2003 |
| WO | WO2014143130 | 9/2014 |
| WO | 2016014469 A1 | 1/2016 |
| WO | 2016014488 A1 | 1/2016 |
| WO | 2017108555 A1 | 6/2017 |

OTHER PUBLICATIONS

"Medela Launches SonataTM Nationwide and Redefines the Breast Pump," Medelabreastfeedingus.com [online] Retrieved from the Internet: <URL: http://www.medelabreastfeedingus.com/media-center/271/medela-launches-sonata-nationwide-and-redefin>, 4 pages, Jan. 3, 2017.

Bartlett et al., "Vibratory Waveform for Breast Pump," U.S. Appl. No. 62/727,909, filed Sep. 6, 2018, 25 pages.

Kent et al., "Importance of Vacuum for Breastmilk Expression," Breastfeed. Med., 3(1):11-19, Mar. 2008.

(56) References Cited

OTHER PUBLICATIONS

Mitoulas et al., "Effect of vacuum Profile on Breast Milk Expression Using an Electric Breast Pump," J. Hum. Lact. 18 (4): 353-360, Nov. 2002.

Bartlett et al., "Breast Pump," U.S. Appl. No. 62/756,370, filed Nov. 6, 2018, 24 pages.

Bartlett et al., "Multi-pump Breast Pump," U.S. Appl. No. 62/727,897, filed Sep. 6, 2018, 44 pages.

Sumiko et al, 変動リズムを含む 吸引によるさく乳の特徴 ( 第 1 報 ) 排乳量の時間的変化と母親使用感 ( 会議録 ) [Study of Breast Pump Suction with Variable Rhythm Temporal Change in Breast Milk Flow and Mothers' Feelings] Japanese Journal of Maternal Health, 59(3)247, 2018 [Poster with English annotations].

International Search Report and Written Opinion in PCT/US2019/049930, dated Dec. 4, 2019, 15 pages.

\* cited by examiner

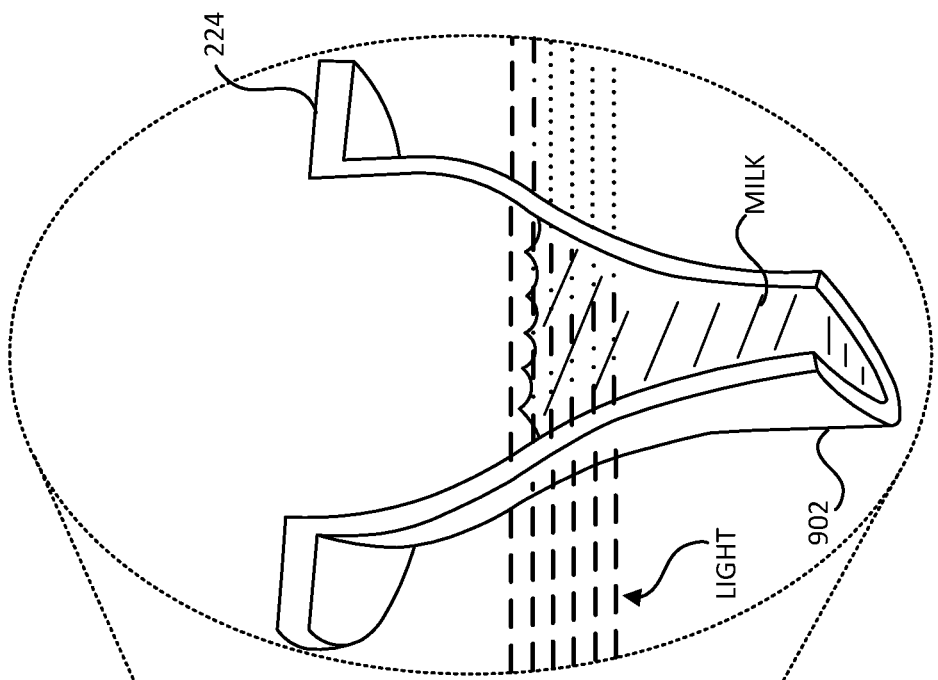
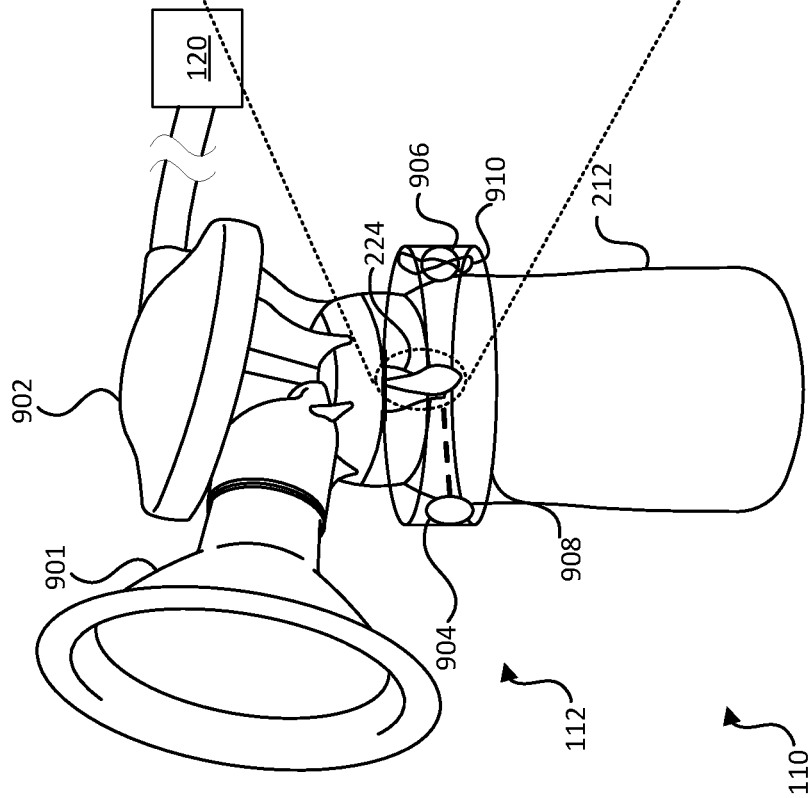
FIG. 9B
FIG. 9A

CLOSED LOOP ELECTRIC BREAST PUMP

CROSS-REFERENCE TO RELATED APPLICATIONS

This application claims priority to U.S. Provisional Application No. 62/727,880, which was filed Sep. 6, 2018, and which is hereby incorporated by references herein in its entirety for any and all purposes.

BACKGROUND

Capturing breast milk is beneficial for mothers who want to provide their infants with natural breast milk. The term "milk" is used herein to refer to liquid expressed by a human or animal breast, which generally includes milk produced by mammary glands. Milk can include colostrum, hindmilk, and foremilk. Breast pumps can be essential tools for mothers to capture milk for later use, which can be especially useful for mothers that are traveling, working, or otherwise away from their infants. Pumping is also useful to relieve engorgement and milk build up in the breast.

Breast pumps traditionally require the user to manually adjust the operating parameters of the pump. A typical breast pump has two distinct modes: the first mode is a stimulation mode to mimic the suckling of the baby to cause the breast to release milk, which is also known as "letdown". The second mode is an expression mode, where the pump creates a vacuum to facilitate the expression of milk into a container, such as a bottle. As used herein, "vacuum" need not refer to a perfect vacuum and instead encompasses a volume having a relatively low pressure (e.g., relative to an environment outside of the volume). Switching between expression and stimulation modes is currently typically performed either through a set timeout or from user input. Other settings that may be available for the user to manually change are vacuum pressure and waveform speed. A primary difference between various breast pumps on the market is the waveform used by the pump. Each mother is unique and would prefer one waveform over the other (and hence prefer one breast pump over the other). It can be difficult for users to properly adjust these manual breast pump settings to quickly and comfortably achieving milk expression.

SUMMARY

Technology disclosed herein relates to breast pumps. Disclosed examples include breast pumps that automatically adjust various parameters of the breast-pump waveform. The adjusting can be configured to, for example, help the mother efficiently express milk by utilizing a closed-feedback system that monitors the flow rate of the expressed milk and total volume of milk expressed.

In an example, there is a breast pump system comprising: a milk collection apparatus comprising a sensor configured to measure fluid within the milk collection apparatus; and a pump console. The pump console can include a pump configured to induce suction at the milk collection apparatus based on one or more pumping parameters and one or more processors. The one or more processors can be configured to: obtain fluid data from the sensor; and modify the one or more pumping parameters based on the fluid data.

The milk collection apparatus can further include a breast shield, and the sensor can be coupled to the breast shield. The system can further include a ring disposed around a portion of the breast shield of the milk collection apparatus, and the sensor can be coupled to the ring. The milk collection apparatus can further include a valve, and the sensor can be coupled to the valve. The breast pump system can further include a light source, and the sensor can include a light detector. The light source and the light detector can be arranged so that light emitted from the light source passes through the valve to reach the light detector. The milk collection apparatus can include a container, and the light source and the light detector can be arranged so that light emitted from the light source passes through the container to reach the light detector. The milk collection apparatus can further include a reflector, and the light source and the light detector can be arranged so that light emitted from the light source passes through the container and is reflected by the reflector to reach the light detector. The sensor can include an electrode. The parameters include but not limited to target pressure, rate of pressure increase, a ramp time, a hold time, a duty cycle, a release time, rate of pressure release or a pumping waveform.

In another example, there is a breast pump system comprising: a milk collection apparatus; a pump console comprising: one or more processors and a pump, wherein the pump is configured to induce suction at the milk collection apparatus based on one or more pumping parameters; and a sensor configured to directly or indirectly obtain measurements regarding the milk collection apparatus. The one or more processors can be configured to: obtain data from the sensor; and modify the one or more pumping parameters based on the data.

The milk collection apparatus can further include a breast shield, and the sensor can be coupled to the breast shield. The milk collection apparatus can further include a valve, and the sensor can be coupled to the valve. The breast pump system can further include a light source, and the sensor comprises a light detector. The light source and the light detector can be arranged so that light emitted from the light source passes through the valve to reach the light detector. The milk collection apparatus can include a container, and the light source and the light detector can be arranged so that light emitted from the light source passes through the container to reach the light detector. The one or more processors can be configured to determine a change in the data over time, and modifying the one or more pumping parameters can be based on the change. The pump console can further include the sensor. The sensor can be a pressure sensor. The one or more processors can be configured to determine a volume of milk within the milk collection apparatus based on a pressure measured by the pressure sensor. The sensor can be a current sensor configured to measure current draw of the pump, and the one or more processors can be are configured to determine a volume of milk within the milk collection apparatus based on the current draw. The parameters can include a pressure, a ramp time, a hold time, a duty cycle, release time, or a pumping waveform.

In another example, there is a method comprising: operating a vacuum pump of a breast pump system using one or more parameters; determining a volume of milk expressed as a result of the operation of the vacuum pump; and automatically modifying the one or more parameters based on the determined characteristic.

Determining the characteristic of the milk can include measuring a pressure with a pressure sensor. Operating the vacuum pump can include operating the vacuum pump through a cycle comprising a ramp period, a hold period, a release period, and a delay period. The release period can further include a first release period, a plateau period, and a second release period and so-forth. The method can include determining a milk ejection pattern of a user of the breast pump system based on the volume of milk expressed. Modifying the one or more parameters can be based on the determined milk ejection pattern.

In yet another example, there is a milk collection apparatus that includes a breast shield for placement on a breast, a container configured to receive milk expressed by the breast, a coupling conduit for coupling the milk collection apparatus to a pump console, and a sensor configured to measure milk within the milk collection apparatus and transmit data to the pump console.

The milk collection apparatus can further include a light source. The sensor can include a light detector. The light source and the light detector can be arranged so that light emitted from the light source passes through milk within the milk collection apparatus to reach the light detector. The milk collection apparatus can further include a ring disposed around a portion of the breast shield. The sensor can be coupled to the ring. The milk collection apparatus can further include a valve, wherein the sensor is configured to measure motion of the valve. The sensor can include an electrode.

BRIEF DESCRIPTION OF THE DRAWINGS

It is believed the present disclosure will be better understood from the following description of certain examples taken in conjunction with the accompanying drawings, in which like reference numerals identify the same elements. The drawings are not intended to be limiting in any way, and it is contemplated that various embodiments can be carried out in a variety of other ways, including those not necessarily depicted in the drawings. The accompanying drawings incorporated in and forming a part of the specification illustrate several aspects of the present disclosure, and together with the description serve to explain the principles of the disclosure; it being understood, however, that the scope of this disclosure is not limited to the precise arrangements shown.

FIG. 9, which is made up of FIGS. 9A and 9B, illustrates an example milk collection apparatus having a sensor configured as an optical sensor.

DETAILED DESCRIPTION

Figure 1:
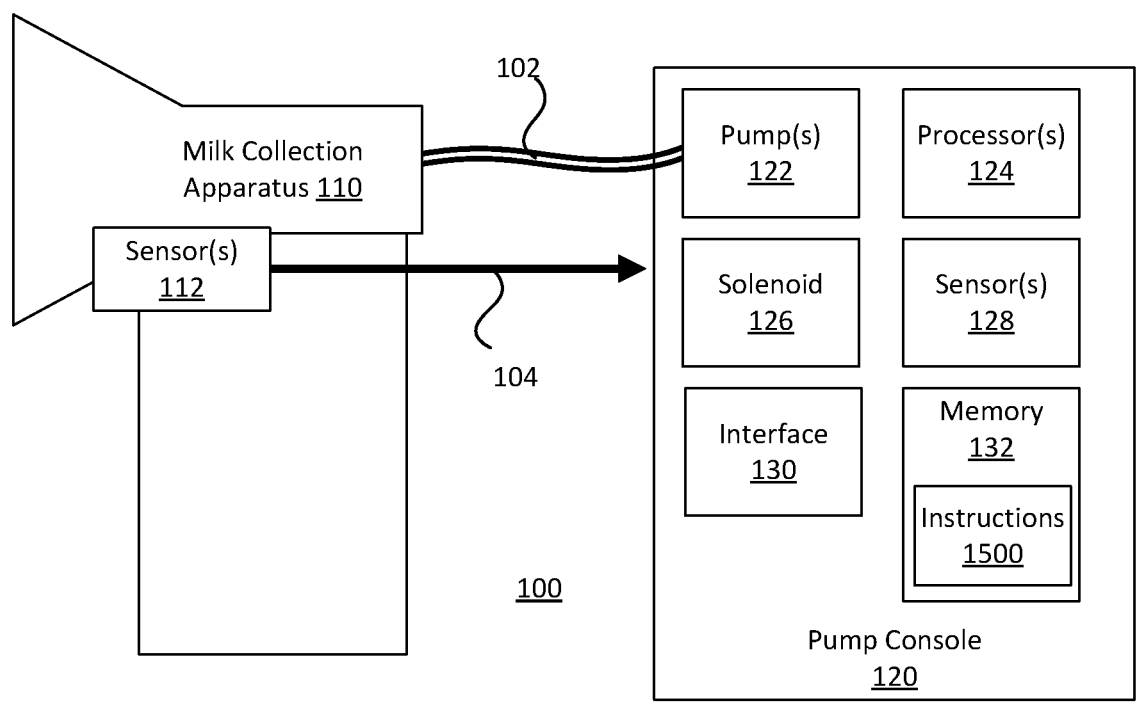
FIG. 1 illustrates an example breast pump system.

Disclosed technology relates to breast pumps. Examples disclosed herein can help breast pump users efficiently express milk by automatically adjusting various parameters of the breast pump. For example, the volume, rate, or other parameters of milk expression can be directly or indirectly measured and pumping parameters can be modified based thereon. Disclosed technologies include technology providing the capability of a breast pump system to directly or indirectly obtain measurements (e.g., milk flow rate) via one or more sensors. Disclosed technologies further include technology for using the measurements to form a closed-loop system with the pump to optimize for desirable qualities (e.g., extraction time, comfort, and quietness). The closed-loop system can include a feedback loop between one or more sensors, one or more processors, and the pumping parameters.

Disclosed examples include various techniques for obtaining measurements, including: measuring milk with a flow sensor (e.g., positioned proximate a breast shield of a milk-collection apparatus), measuring accumulated milk proximate a valve of the milk-collection apparatus, measuring back-pressure on a diaphragm at the pump side as a surrogate of accumulated milk volume in the valve, and measuring an effort of a vacuum pump (e.g., by measuring current draw or a duty cycle). Other techniques are also possible, including the use of sensors to measure an accumulation of milk in a collection vessel and the use of a pressure sensor in line with the vacuum pump.

Example sensors include one or more sensors associated with a breast shield, anterior chamber, valve, or container of the milk collection apparatus. For example, the one or more sensors can include optical sensors, electrical sensors, mechanical sensors, other kinds of sensors, or combinations thereof. An optical sensor can include an optical emitter and an optical receiver. The amount of light blocked or otherwise affected (e.g., by milk, a distended nipple, or motion of a valve) can be used to directly or indirectly obtain measurements regarding an amount of milk obtained or comfort of the user (e.g., where the optical sensor is configured to detect a distended nipple). In another example, the optical sensor can be a camera to obtain one or more images that are analyzed to determine measurements (e.g., an amount of milk in a container). A mechanical sensor can be a flow meter that directly or indirectly contacts the expressed milk to obtain flow measurements. An electrical sensor can include one or more electrodes extending along a nipple channel of a breast shield of the milk collection apparatus. The one or more electrodes may be shielded to prevent or reduce disturbance from the outside environment (e.g., a user's hands). The one or more electrodes can measure a change in capacitance to determine milk flow rate or other characteristics (e.g., nipple distention, which is correlated to nipple pain). As milk or a nipple move proximate the electrode, a dielectric constant can be increased, which results in a measurable increase in capacitance.

The one or more sensors used to obtain the data can be part of a discrete component configured to couple with another component of the breast pump system or the one or more sensors can be built into (e.g., integral with) one or more components of the breast pump system. The one or more sensors can be external to the components of the system and can include, for example, a smart bottle, an external scale, or a video camera.

The data from one or more of the sensors can be obtained and used by one or more processors to apply some type of corrective action, such as a change in parameters or an alert being provided to a user. The processor can be within a pump console (e.g., a component that houses the pump) or external to the pump console. In some examples, a consumer device (e.g., a smartphone, tablet, or laptop) can perform at least some of the processing and modify one or more parameters of a pump. The processor can facilitate proper pressure being presented at the breast. The processor can adjust the various parameters of the waveform and can measure the resulting effect on the milk flow rate. The system can take into account potential user discomfort when modifying parameters (e.g., the parameters can be kept within safety or comfort tolerances). The system can also take into account noise when modifying parameters (e.g., to limit an amount of noise made by the system when in operation). For example, the pump can be configured to operate when vacuum is maintained. This can be helpful for users that pump in the same room as their baby, as a breast pump pumping while not attached to the breast can be very loud. Likewise, if the breast shield is removed from the breast, the breast pump system can detect the removal and can automatically stop the pumping session. The technology herein can further facilitate determining whether the system is functioning properly. For example, the system can determine vacuum loss within the system. As a result of detected vacuum loss, the pump can alert the user and potentially indicate where the pump system is not assembled correctly or if any components are not attaching well to each other within the assembly. The processor can take into account an altitude at which the pump is operating and whether the user is using single pump or double pump system. While many examples herein are described in the context of a single milk collection apparatus being used, disclosed examples can be applied to breast pump systems having two milk collection apparatuses. In examples with multiple milk collection apparatuses, different sensor data can be collected and different parameters can be determined for each milk collection apparatus, so differences in milk expression on a breast-by-breast basis can be determined and accounted for (e.g., by having a different pumping waveform used by each breast). Alternatively, one or more sensors can be used to generate data and pumping parameters shared by each breast.

With the breast and breast pump acting as a closed-loop system, the rate of milk expression measured by the sensors or via another technique can be a feedback signal based on which parameters can be changed to optimize for increasing an amount of milk obtained during a session or decreasing an amount of time taken to obtain a particular amount of milk (e.g., enough milk to fully empty a user's breast). The optimization can include optimizing for reduced hold time.

To determine when the milk extraction has completed for that cycle, the system can measure the rate of change of pressure and when the rate is smaller than a threshold the breast pump can then begin the release phase without delay (or without substantial delay). Improvements to milk extraction can be further based on a particular milk expression pattern of the user. For example, research indicates that mothers can be categorized into four different milk ejection patterns, which are described in more detail in FIG. 20 herein. See Kuroishi Sumiko, et al., "Study of Breast Pump Suction with Variable Rhythm Temporal Change in Breast Milk Flow and Mothers' Feelings", Japanese Journal of Maternal Health, 59(3), 247 (2018), which is hereby incorporated by reference herein in its entirety for any and all purposes. Further, some mothers express milk faster when the pump waveform is variable and others express milk faster when the waveform is constant. Disclosed examples can allow the breast pump to automatically determine which kind of waveform can express milk faster for a particular user. For example, the rate of milk expression during use of a constant waveform can automatically be compared against the rate of milk expression during use of a variable waveform.

In one example optimization technique, a PID (Proportional Integrative Derivative) loop is used that can include first and higher order PID loops. To increase flow rate, the system can modify pumping parameters, such as by modifying pressure, ramp time, hold time, duty cycle, pumping waveform, other parameters, or combinations thereof. The system can also use any of a variety of machine-learning or artificial intelligence algorithms (e.g., simulated annealing or genetic algorithms) to facilitate processing the data or selecting parameters. Through the use of such techniques, parameters can be optimized for the particular user to improve, for example, a rate of milk expression. Where a PID controller is used, the system can first ensure that the tunable parameters (e.g., rise time, hold time, pressure, and cycle time) are in negative feedback (e.g., a detected decrease in milk flow rate can result in a proportional increase in pressure to attempt to increase the milk flow rate). The PID controller can attempt to maintain a target milk flow rate. The PID controller can also be set to maintain a target pressure on the breast. For example, when the breast is emptied, the empty volume in the anterior chamber is increased, thereby decreasing overall pressure to the breast.

The maximum rate at which pressure changes over a fixed time can be set by a parameter or by the pump motor itself. By driving the motor with a pulse-width modulation, the rate at which the pressure rises over time can be controlled. Disclosed examples can advantageously allow the system to determine whether a target pressure is reached. Absent a closed feedback system, the target pressure can be achieved by running the motor at a 100% duty cycle for a fixed, pre-determined amount of time found by trial and error, which can be difficult. With the closed feedback system, the system can control the rise time and the target pressure independently. The closed-feedback system can adjust the rise time rate by controlling the pulse width modulation, and stop running the motor once the target pressure is reached.

As described above, a breast pump system can include a variety of components acting as sensors that can produce data to control pumping parameters to improve the function of the system. Breast pump systems can come in any of a variety of configurations. An example breast pump system that can operate as a closed-loop system is described in FIG. 1.

Breast Pump System

FIG. 1 illustrates an example breast pump system 100. The pump system includes two primary components connected by a tube 102: a milk collection apparatus 110 and a pump console 120. Although the figure illustrates the milk collection apparatus 110 and the pump console 120 being discrete components relatively remote from each other, they need not be. In certain implementations, the breast pump system 100 can have, for example, the pump console 120 directly coupled to the milk collection apparatus (e.g., the milk collection apparatus 110 and the pump console 120 can be part of a same housing or structure).

The milk collection apparatus 110 is a component of the breast pump system 100 configured to apply suction to a breast to collect milk. An example implementation of the milk collection apparatus 110 is described in more detail in FIG. 2. In the illustrated configuration, the milk collection apparatus 110 includes one or more sensors 112. The sensors 112 are described in more detail herein and can be configured to measure milk within a flow path of the milk collection apparatus 110. The flow path can include the path the milk takes from the breast to a container of the milk collection apparatus 110. The data from the one or more sensors 112 can be transmitted to the pump console 120 for processing via a wired or wireless connection 104. In addition to measuring milk within a flow channel, one or more of the sensors 112 can be configured to determine, for example, whether a nipple has distended too far forward into the milk collection apparatus 110 (e.g., which may be an indicator of pain). The sensors 112 can be configured to not impede a traditional pumping workflow (e.g., cleaning, assembly, and use of a breast pump). Further, the sensors 112 can be configured to not come in direct contact with fluids or, if the sensors do come in contact with fluids, the sensors 112 can be biocompatible and easy to sterilize and clean.

The pump console 120 is a component of the breast pump system 100 configured to induce suction in the milk collection apparatus 110. In the illustrated configuration, the pump console 120 includes a vacuum pump 122 coupled to the milk collection apparatus 110 via the tube 102. While typically referred to herein as a singular vacuum pump, the vacuum pump, the milk collection apparatus 110 can include multiple pumps 122 and references herein to a single pump can be replaced with multiple pumps. An example implementation of the pump console 120 and its components (including multiple pumps 122) is described in U.S. 62/727,897, which is tilted "Multi-Pump Breast Pump", and which is hereby incorporated by reference herein in its entirety for any and all purposes. Other example implementations of the breast pump system 100 are described in U.S. Pat. No. 8,545,438, which is titled "Breast Pump" and which is hereby incorporated by reference herein in its entirety for any and all purposes. The pump 122 and other components of the breast pump system 100 can be controlled by one or more processors 124.

The one or more processors 124 are one or more electronic components that control one or more other components of the pump console 120. The one or more processors 124 can, for example, control the function of the pump 122. The one or more processors 124 can be configured to obtain input (e.g., from the one or more milk collection apparatus sensors 112 and from the one or more pump console sensors 128), process the input, and take one or more output actions based thereon. The output actions can include modifying parameters that the one or more processors 124 use to control components of the system 100. The one or more processors 124 can include one or more microprocessors, application-specific integrated circuits, field programmable gate arrays, other components, or combinations thereof. The one or more processors 124 can obtain input from the interface 130. The one or more processors 124 can be configured to execute instructions stored in the memory 132 to perform operations. The processor 124 can modify parameters of the breast pump system 100 to facilitate the expression of milk from the breast The pump console 120 can further include a solenoid 126, one or more sensors 128, an interface 130, and memory 132.

The solenoid 126 is a component of the vacuum pump console 120 (or the pump 122 itself) configured to actuate a release valve to release some or all of the vacuum created by the vacuum pump 122. The solenoid 126 can be controlled by the processor 124 to open, partially open, or close the release valve.

The one or more sensors 128 are components of the pump console 120 configured to generate data. In an example, the one or more sensors 128 can include a pressure sensor configured to measure a pressure or amount of the vacuum created by the vacuum pump 122. In addition to or instead of pressure sensors, the one or more sensors 128 can include time sensors, location sensors (e.g., GPS-based location), temperature sensors, altitude sensors, humidity sensors, accelerometers, impedance sensors, light sensors, other sensors, or combinations thereof.

The interface 130 can include one or more components configured to receive input or provide output. The interface 130 can include, one or more components to receive input from a user (e.g., via one or more switches, buttons, touch interfaces, pointer devices, other components, or combinations thereof), provide input to a user (e.g., via one or more displays, lights, speakers, other components, or combinations thereof), and one or more components for communicating with other devices via a wired (e.g., via an Ethernet connection, a serial interface connection, a parallel interface connection, other connections, or combinations thereof) or wireless (e.g., via a radiofrequency connection, such as WI-FI, BLUETOOTH, other wireless radiofrequency connections, or combinations thereof). Disclosed examples can further allow for new user controls for the breast pump as part of the interface 130. For instance, the processor 124 can be configured to detect a pressure change caused by a user squeezing a component of the milk collection apparatus 110 (e.g., a breast shield thereof) and, in response, start or stop the pump 122.

The memory 132 is a processor-readable storage media operable to store information, such as data or instructions. The information stored on the memory 132 can be accessed and processed by the one or more processors 124. The memory 132 can include random-access memory, read-only memory, programmable read-only memory (e.g., electronically-erasable programming memory), volatile memory, or non-volatile memory. The memory can use any of a variety of technologies including, for example, optical, magnetic, spinning disk, or solid-state, among other technologies. The memory 132 can include transitory or non-transitory computer readable mediums.

The milk collection apparatus 110 and the pump console 120 can be implemented in any of a variety of forms. An example implementation of the milk collection apparatus 110 is described in FIG. 2.

Figure 2A:
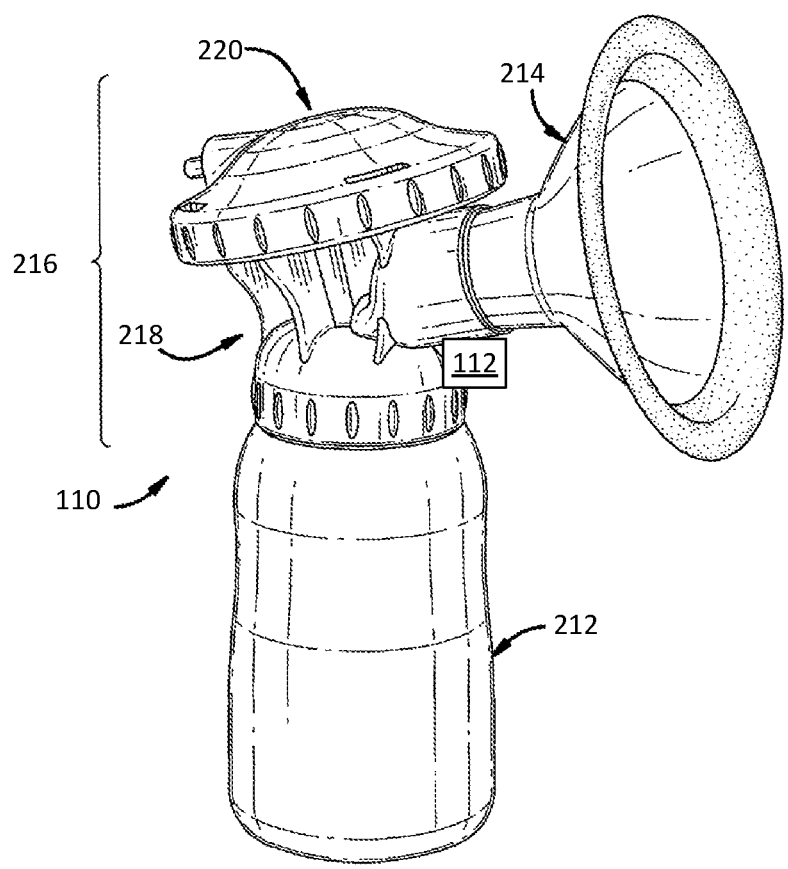
FIG. 2, which is made up of FIGS. 2A and 2B, illustrates an example implementation of a milk collection apparatus.
Figure 2B:
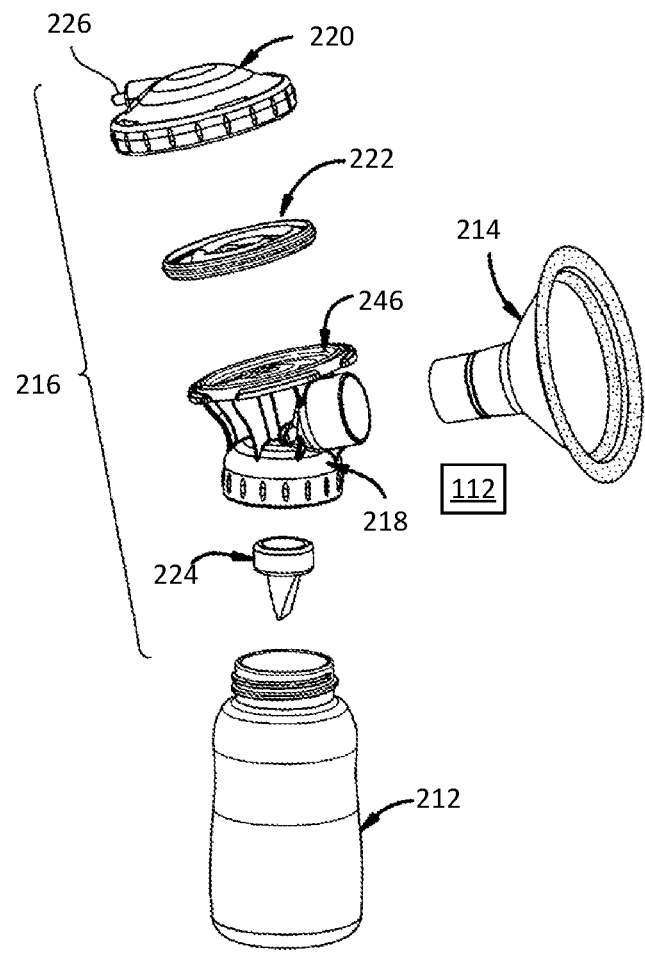

FIG. 2, which is made up of FIGS. 2A and 2B, illustrates an example implementation of a milk collection apparatus 110. As illustrated, the milk collection apparatus 110 can include a container 212 and a suction transfer assembly 216. The container 212 is a component for receiving milk. The container 212 can take any of a variety of forms, such as a bottle, syringe, bag, or other type of void space. The suction transfer assembly 216 includes a breast shield 214 (which can also be referred to as a flange) for placement on a breast, as well as an anterior chamber defined within a suction housing 218, a vacuum housing 220, a diaphragm 222, and a valve 224. The diaphragm 222 can be a flexible membrane or other component separating an anterior chamber of the milk collection apparatus 110 from a pump volume while still allowing pressure changes to be communicated across. Some implementations of the breast pump system 100 can lack a diaphragm 222.

The valve 224 can be a component separating the anterior chamber from the container 212. The valve 224 can be a one-way valve, such as a duckbill valve. The valve 224 can take any of a variety of forms, such as a flow restrictor valve, a spring driven valve, a hydraulic piston, or other types of pressure regulating valves. The suction transfer assembly 216 can transfer pressure through the diaphragm 222. And the suction transfer assembly 216 can include a coupling conduit 226 for coupling the milk collection apparatus 110 to a pump console 120 for modifying the pressure. In some examples, the vacuum housing 220 can include or be configured as a pressure regulation feature. The pressure regulation feature can be adjustable by the user such that different dimensions of pressure regulation features can be attached as the user desires to provide for a higher or lower maximum vacuum dimension allowed by the breast pump system 100. Additional details regarding an example milk collection apparatus 110 are described in U.S. Pat. No. 8,444,596, which is titled "Breast Milk Collection Apparatus and Components Thereof" and which is hereby incorporated by reference herein in its entirety for any and all purposes.

The milk collection apparatus 110 can cooperate with the pump console 120 to cause milk expression from a breast placed in the breast shield 214. An example operation of the breast pump system 100 is described in FIG. 3.

Figure 3A:
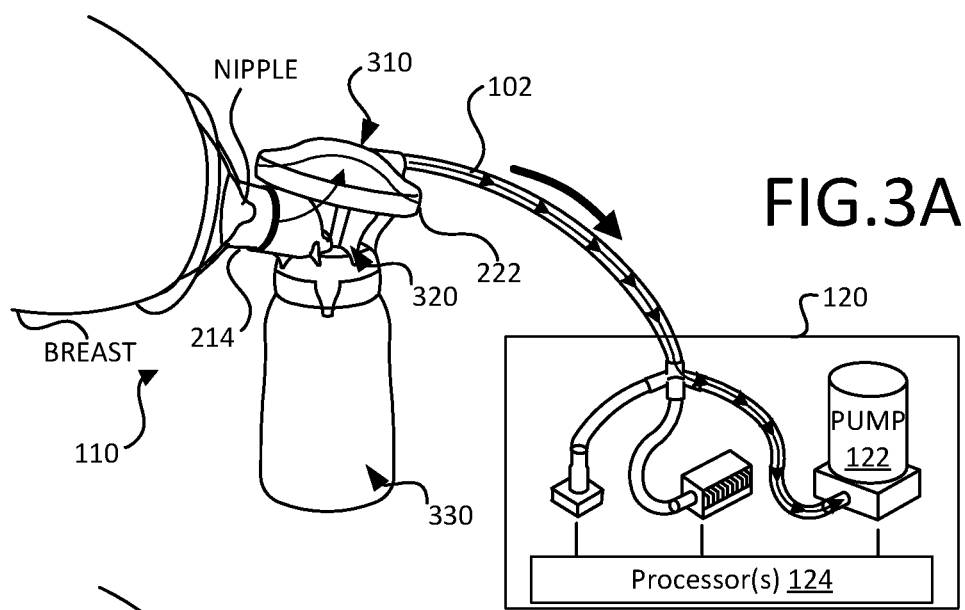
FIG. 3, which is made up of FIGS. 3A, 3B, and 3C, illustrates an example operation of a breast pump system.
Figure 3B:
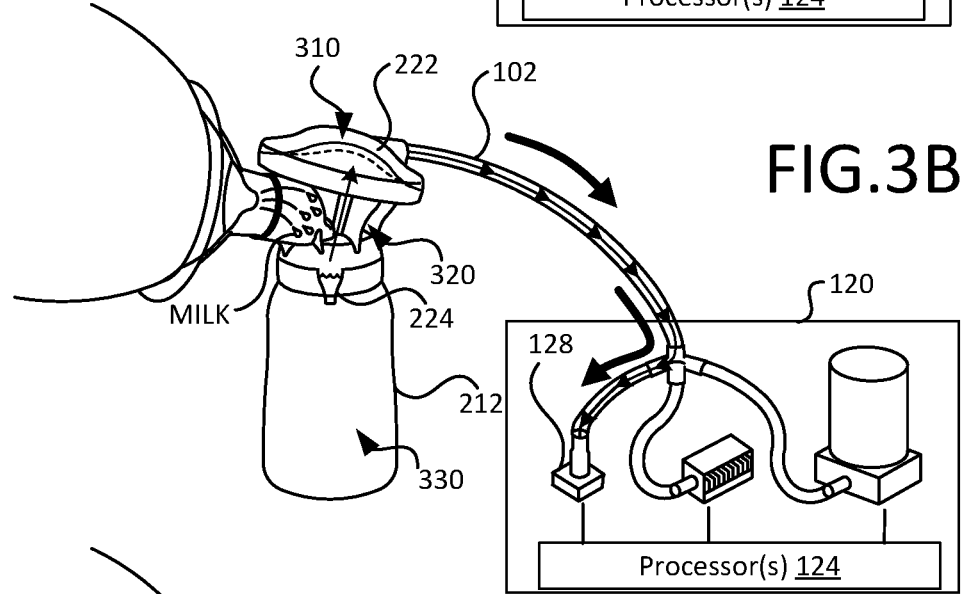
Figure 3C:
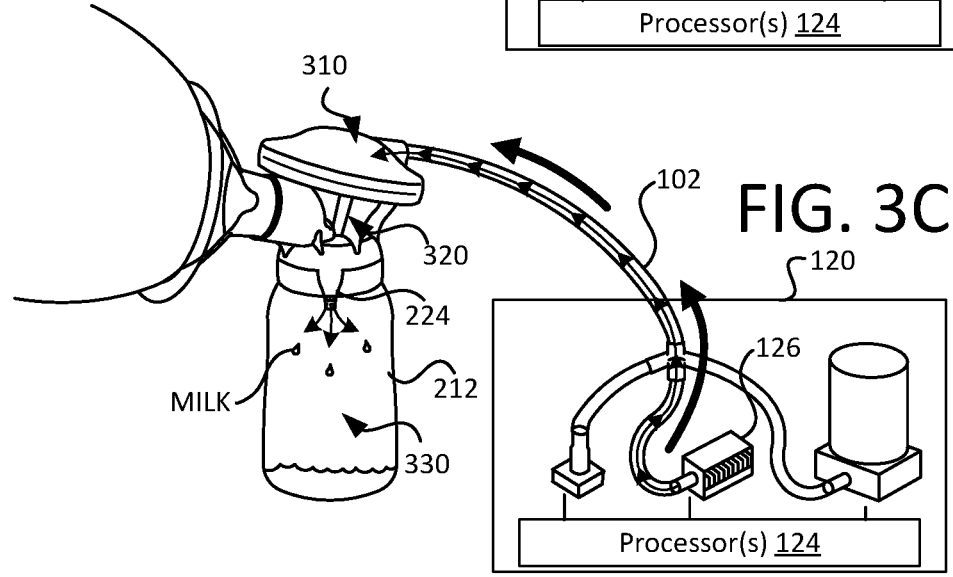

FIG. 3, which is made up of FIGS. 3A, 3B, and 3C, illustrates example operation of the breast pump system 100. As illustrated, the breast pump system 100 can define a pump volume 310, an anterior chamber 320, and a container volume 330. The anterior chamber 320 can be a volume at least partially bounded by a breast in which pressure is modified to stimulate the breast and cause the expression of milk into the anterior chamber 320. The anterior chamber 320 can be defined in part by the diaphragm 222, which can separate the anterior chamber 320 from the pump volume 310. The diaphragm 222 can be flexible such that pressure changes in the pump volume 310 affect the pressure of the anterior chamber 320. For example, the diaphragm 222 can contribute to a seal (e.g., a hermetic seal) that allows pressure changes in the pump volume 310 to be communicated to the anterior chamber 320. The pump volume 310 is the volume that the pump 122 directly affects in order to cause pressure changes in the anterior chamber 320. The pump volume 310 can include a portion of the milk collection apparatus 110 that is "above" the diaphragm 222 (e.g., where the anterior chamber 320 can be considered "below" the diaphragm 222) as well as the tube 102 and a portion within the pump console 120 that includes the pump 122. The pump 122 can be activated to reduce pressure in the pump volume, and a release valve (e.g., controlled by the solenoid 126) can be opened to allow pressure in the pump volume 310 to begin to equalize with a surrounding environment. The illustrated anterior chamber 320 is separated from the container volume 330 via the valve 224. The valve 224 can be a one way valve (e.g., a duckbill valve) that allows fluid (e.g., air and milk) to flow into the container 212 but not to flow back into the anterior chamber 320. Beneficially, this separation can allow for the anterior chamber 320 to be substantially smaller than the volume that would typically be necessary for collecting expressed milk during a pumping session. This smaller volume of the anterior chamber 320 is more easily affected by the pressure changes in the pump volume 310.

FIG. 3A illustrates a breast and nipple received within the breast shield 214. The pump 122 can receive a control signal from the processor 124 that causes the pump 122 to activate to remove air from the pump volume 310 or otherwise reduce the pressure in the pump volume 310. As the pressure is reduced in the pump volume 310, the diaphragm 222 deforms and causes a reduction in pressure in the anterior chamber 320, which induces suction at the breast.

FIG. 3B illustrates the change in pressure causing milk to be expressed in the anterior chamber 320 of the milk collection apparatus. The change in pressure can further cause the valve 224 to close and seal off the anterior chamber 320 from the container volume 330. As milk accumulates in the anterior chamber 320, the milk displaces volume, which causes an increase in pressure in the anterior chamber 320 and pushes the diaphragm 222 upwards. This increase in pressure caused by the milk can be communicated to the pump volume 310 via the diaphragm 222 and sensed by a sensor (e.g., one or more sensors 112 or one or more sensors 128 of the breast pump system 100 as is described in more detail herein). For example, the pump console 120 can detect the pressure change to infer an amount of milk expressed, which can be used by the processor 124 to help determine if letdown has occurred, if the breast is out of milk, or if more stimulation is possible. By integrating the accumulated milk in each cycle, the pump console 120 (e.g., the processor 124 thereof) can estimate the total amount of milk pumped in the cycle and the session (which can include multiple cycles). A sensor can measure or infer a change in pressure as milk is expressed from the breast fills the anterior chamber 320 (e.g., prior to release of the pressure and opening of the valve 224 to allow the milk to flow into the container 212). For example, depending on the variation in pressure relative to power draw and or time, the breast pump system 100 can determine how the volume in the anterior chamber changes and therefore correlate to how much milk has been expressed into the anterior chamber 320 as a surrogate method of determining milk flow.

FIG. 3C illustrates the release of pressure via the solenoid 126. For example, the processor 124 can send a control signal that causes the solenoid 126 to at least partially open a release valve to reduce the vacuum (e.g., allow the pressure to increase) in the pump volume 310. The change in pressure in the pump volume 310 results in an increase in pressure in the anterior chamber 320, which allows the valve 224 to open. The opening of the valve 224 allows the milk volume that was collected in that cycle to drop into the container 212.

The operation cycle described in FIG. 3 can be repeated several times until a desired amount of milk is expressed and collected in the container 212. As described above, data obtained from sensors 112, 128 or elsewhere can be used by the one or more processors 124 of the pump console 120 to modify pumping parameters that can affect the ability of the system 100 to cause milk expression. For example, during the operation cycle, pressure within the system 100 can be monitored and used to determine an amount of milk expressed.

Determining Milk Expression Using Pressure

As described above, the breast pump system 100 can define three primary volumes: the pump volume 310, the anterior chamber 320, and the container volume 330. A measured pressure in the pump volume 310 correlates to the volume of the anterior chamber 320. The resting pressure in the anterior chamber 320 can equal the resting pressure on the pump volume 310. As the pump 122 is activated (e.g., with the release valve closed and the valve separating the anterior chamber 320 from the container volume 330 being closed), pressure decreases in the pump volume 310, which is communicated to the anterior chamber 320 via the diaphragm 222, which results in milk extraction from the breast into the anterior chamber 320. The extracted milk is temporarily confined within the anterior chamber 320 because the valve 224 is closed. The valve 224 can remain closed during a hold period of the pump waveform. During the hold period, the hold pressure in the anterior chamber 320 is equal to the hold pressure in the pump volume 310. Based on the ideal gas law (i.e., PV=nRT, where P is the pressure, V is the volume, n is the number of moles, R is the ideal gas constant, and T is the temperature), it can be assumed that temperature change is minimal and the displaced volume by the breast during the hold period is constant. The extracted milk constitutes a decrease in volume in the anterior chamber 320 by a Δv, which will result in an increase in pressure by ΔP in both the anterior chamber 320 and the pump volume 310. This increase in pressure can be measured by an inline pressure sensor (e.g., sensor 128), which can correspond to the milk during the hold phase. The pressure sensor can take any of a variety of forms, such as a MEMS (microelectromechanical systems) sensor, a deflection-based sensor, a strain-based sensor, a magnetic sensor, other sensors, or combinations thereof. Since the system 100 can determine a waveform cycle period, the flow rate can be calculated. As the pump 122 transitions to vacuum-release, pressure in both the anterior chamber 320 and the pump volume 310 is equalized, the valve 224 opens allowing the temporarily-confined milk to flow into the container volume 330, thereby resetting the system 100 to be ready to measure flow rate for a next waveform cycle.

Some implementations of a breast pump system 100 can lack a diaphragm 222. In such examples, the pump 122 can directly affect the pressure in the anterior chamber 320 without a diaphragm 222 communicating the pressure change. In such implementations, it can still be helpful to distinguish between the pump volume 310 (e.g., a volume from the coupling conduit 226 to the pump 122) and the anterior chamber (e.g., a volume between the valve 224 and the coupling conduit 226), but rather than pressure changes being communicated via the diaphragm 222, the pressure changes in the pump volume 310 directly affect the pressure of the anterior chamber 320.

In some examples, during a stimulation phase where no milk is expressed, pressure in the pump volume can be measured using the sensor 128 to serve as a base measurement of pressure without milk present. The pressure can be measured at different points in a waveform cycle and signal processing can be used to measure the effects of the changed pressure (e.g., due to changes in volume in the anterior chamber 320) from the expressed milk. As there can be multiple letdowns within a pumping session, the system 100 can use cycles within the first letdown as a baseline to optimize for future letdowns within a current session or future sessions by storing a pressure profile or tuned waveform parameters in memory for use during future letdowns. Signal processing can include averaging pressure waveforms within one or more cycles (e.g., to create a running average) to increase a signal-to-noise ratio. Other methods include creating a model (e.g., a mathematical or statistical model) using historical data of milk expression for the individual user, where a function takes a pressure as input and produces a flow rate as output.

A more complicated signal processing method can use sigma-delta modulation. The pump 122 can be driven using a pulse-width modulation signal sent from the processor 124. A pressure provided by the pump 122 can be affected by a duty cycle of the signal. Sigma-delta modulation can be used to determine how long the pump 122 needs to be active to maintain a set pressure (e.g., the duty cycle needed to maintain a particular pressure in the pump volume 310 during a hold period). Since the pump volume 310 likely has at least some leakage, the pump 122 can be active even during a holding period to maintain a set pressure. As milk is expressed into the anterior chamber 320, pressure increases, which can reduce the amount of time needed to turn the vacuum on to maintain the set pressure. The amount of time the pump 122 is in an on state (e.g., a change in the duty cycle needed to maintain pressure) can be correlated to the amount of accumulated milk within the anterior chamber for each cycle. A sigma-delta count can be used stand-alone measure or as an additional factor for an algorithm to increase the accuracy of prediction for the milk flow rate or the total accumulated volume.

In addition to or instead of the use of pressure or pump 122 characteristics, other sensors can be used to obtain data regarding a pumping session. Example implementations of the sensors 112, 128 are described in FIGS. 4-14.

Sensors

Various sensors can be used by the breast pump system 100 to obtain data usable to modify pumping parameters. An example sensor is an acoustic sensor (e.g., disposed on the side of the container 212) that can indicate a change in the sound produced as milk begins to flow and drip from the valve 224 into the collection compartment. This change in sound can indicate that letdown occurred and, in response thereto, the processor 124 can cause the pump 122 to switch from a stimulation phase (e.g., having a relatively rapid cycle) to an expression phase (e.g., having a longer cycle time than the stimulation phase). A change in sound can also indicate a reduction in flow rate. For example, the sensor 112 can take the form of a microphone configured to obtain sound indicative of milk flowing from the anterior chamber 320 to the container 212. The sound obtained from the sensor 112 can be obtained and analyzed, such that if the sound obtained from the sensor indicates that flow is relatively low or is decreasing at a particular rate, then the processor 124 can cause the pump 122 can begin a new stimulation phase.

Sensors can also be placed on or proximate the breast, which can allow the pump system 100 to determine if the fluid retained in the breast is indicative of there being a potential for a second letdown with more expression of milk or if the breast is empty or near empty with little additional reason to continue pumping. Such sensors can also be configured to determine the amount of engorgement in the breast and the amount of milk remaining in the breast. An engorged breast tends to have less breast movement when the vacuum is applied compared to a nearly-empty breast. This breast movement can be detected by the pressure sensor and using an algorithm determine the amount of milk remaining in the breast. In some examples, an estimated amount of milk remaining in the breast can be used to determine a milk ejection pattern of the user. In addition or instead, such data can be used to modify pumping parameters. Sensors can be, for example disposed at a portion of the breast shield 214 that is likely to contact breast tissue. In addition or instead, such sensors can detect if the user's skin is dehydrated, stiff, or otherwise indicative of too much or too little fluid within the body. Such data can be used as an indication of dehydration or low milk supply. With the information, the processor 124 can predict the remaining time to fully express the milk from the breast. Further, the determination can facilitate the user knowing if the breast is substantially empty, which can reduce the incidence of mastitis.

Sensors can further include a location-determining sensors (e.g., via GPS) for determining a likely altitude (and therefore a likely atmospheric pressure). In addition or instead, systems can include an external pressure sensor to determine the atmospheric pressure directly. Examples can further include a clock or time-input mechanism, which can be used to determine a current time of day. The time of day can be used to recognize if a user is pumping in the morning, midday, evening, night, or any other time. The time of day can then be correlated to the pumping pattern for that user based on prior daily patterns of pumping at those times. In some instances, longer suction waveforms can be used to facilitate the expression of milk at later times of the day as more retained milk is held in the back parts of the breast. Additionally, different times of the day can indicate different cycles of stimulation phase and expression which can be helpful to create more letdowns and produce more milk. Wavelengths can be modulated in accordance with time or any other variables incorporated into a processor to adjust the wavelengths of the pumping curve within a single pumping session or even between pumping sessions at different times of the day or year. In addition, temperature sensors can be included in the system, such as ambient air temperature sensors or skin temperature sensors as an indicator of receptivity to letdown or provide another parameter. Such data can also be used to determine which suction pattern should be used by the breast pump system 100 given those environmental parameters (e.g., to encourage fast and comfortable pumping).

Other sensors for electrical impedance, capacitance, resistance, ultrasonic wave measurement, and or electrical nerve conduction or blood flow can help determine if there is letdown, such that electrical signals are firing which can be measured. Further, the opening of the milk ducts can be directly measured by changes in features such as but not limited to diameter or dielectric constants.

Among the kinds of sensors that can be used are electrode-based sensors (see, e.g., FIG. 4, FIG. 7, and FIG. 14), optical sensors (see, e.g., FIG. 5, FIG. 9, and FIG. 13), and magnetic sensors (see, e.g., FIG. 7), among others. The sensors 112, 128 can be disposed in any of a variety of locations, such as proximate the breast shield 214 (See, e.g., FIGS. 4-6), proximate the valve 224 (See, e.g., FIGS. 7-9), proximate the container 212 (see, e.g., FIG. 12 and FIG. 13), proximate the diaphragm 222 (See, e.g., FIG. 14), in other locations, or combinations thereof. In addition sensors that are separate from the milk collection apparatus 110 and the pump console 120 can be used, such as via a consumer computing device (see, e.g., FIG. 10) or a separate measuring device (see, e.g., FIG. 11). These examples implementations are described in further detail in conjunction with FIGS. 4-14, below.

Figure 4:
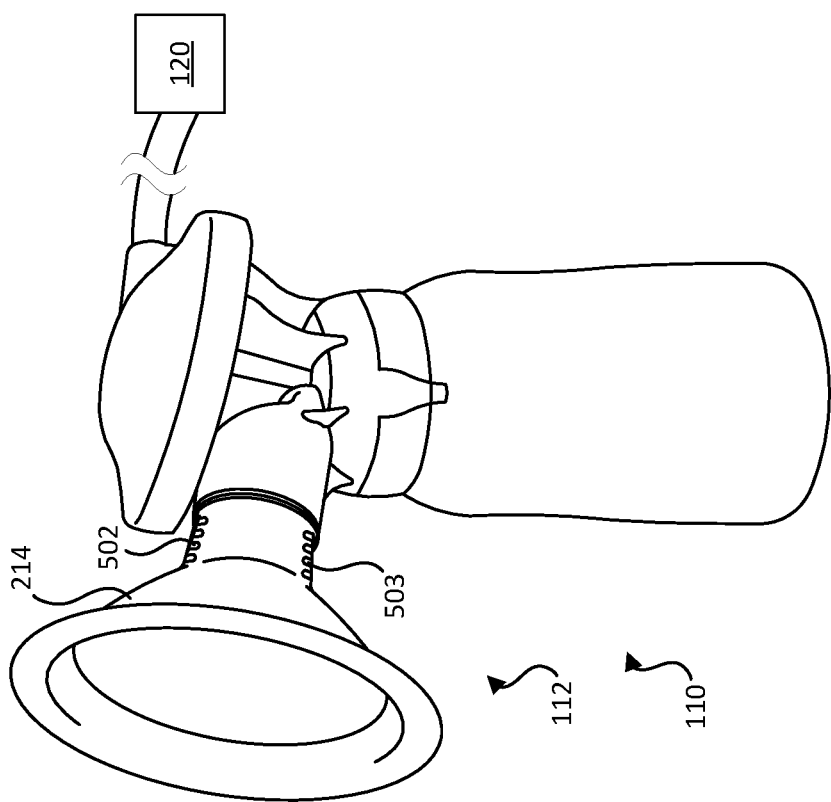
FIG. 4 illustrates an example milk collection apparatus having one or more sensors configured as electrodes.

FIG. 4 illustrates an example milk collection apparatus 110 having one or more sensors 112 configured as electrodes. In an example, the electrodes can be configured as a capacitive flow meter with impedance sensing (both real and imaginary) from direct current to radiofrequency. In particular, the illustrated milk collection apparatus 110 includes a sensor 112 that includes an excitation electrode 402 and a sensing electrode 403. As illustrated, the electrodes 402 403 are disposed across from each other along a fluid flow path of the milk collection apparatus. In particular, the illustrated configuration shows the electrodes 402, 403 disposed on or in the breast shield 214. In other examples, the electrodes 402, 403 can be disposed elsewhere, such as proximate the anterior chamber or the valve 224. The excitation electrode 402 and the sensing electrode 403 can cooperate to generate and sense electric fields to measure fluid flow across a flow channel of the milk collection apparatus 110. For example, the presence of milk can affect the electric field. The effects of the milk on the electric field can be sensed and used to modify operation of the pump 122 or other components of the breast pump system 100. As such, the electrodes 402, 403 can cause a signal to be sent to the processor 124. The data can be used by the processor 124 to change pumping parameters (e.g., different types of vacuum patterns, actuation levels, time scales, or oscillation patterns).

In addition to or instead of the sensors 112 configured to detect properties of milk flowing into the collection apparatus 110, the sensors 112 can also be configured to detect the presence of nipple or breast tissue in the apparatus 110 and measure the distance the tissue distends into the apparatus 110 when suction is applied.

Figure 5:
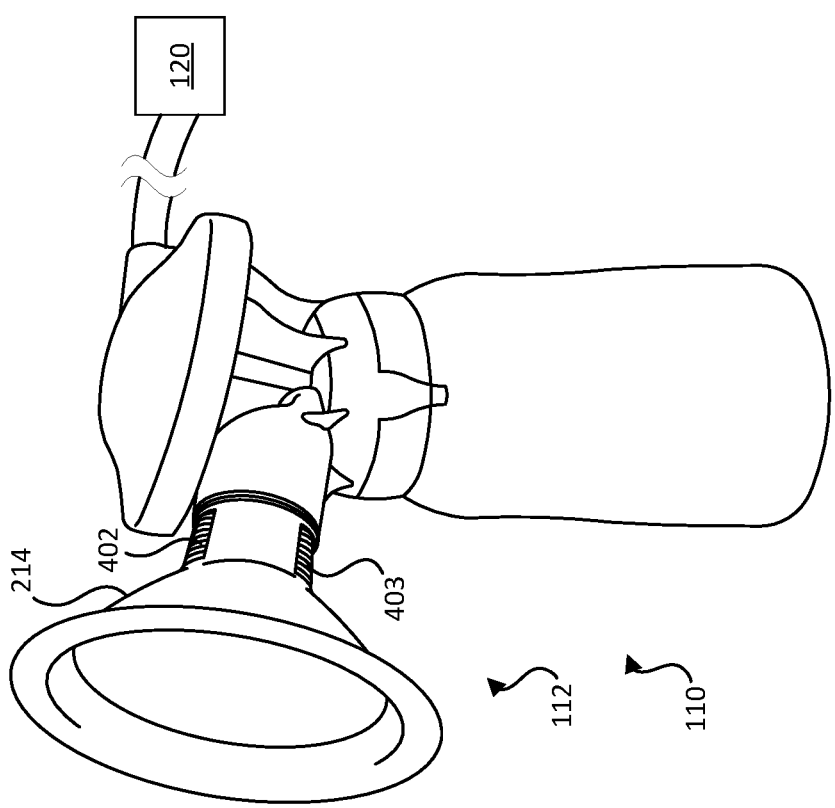
FIG. 5 illustrates an example milk collection apparatus having one or more sensors configured as optical sensors.

FIG. 5 illustrates an example milk collection apparatus 110 having one or more sensors 112 configured as optical sensors. In an example, the optical sensors can be configured to provide an inline flow meter. The one or more optical sensors 112 include one or more light sources 502 and one or more photodetectors 503. The one or more light sources 502 and one or more photodetectors 503 can cooperate to measure whether and to what extent material passes between the light sources 502 and the one or more photodetectors 503. For instance, the one or more light sources 502 can be configured as one or more visible or non-visible spectrum light emitting diodes positioned on the breast shield 214, and the one or more photodetectors can be positioned such that milk flowing through the collection apparatus 110 disrupts a signal measured by the one or more photodetectors 503. The effect on the light received by the photodetectors 503 can be measured to facilitate the measurement of an amount of milk or a milk flow rate. While the above example is described in the context of visible light, non-visible wavelengths can be used in addition to or instead of visible light.

Figure 6:
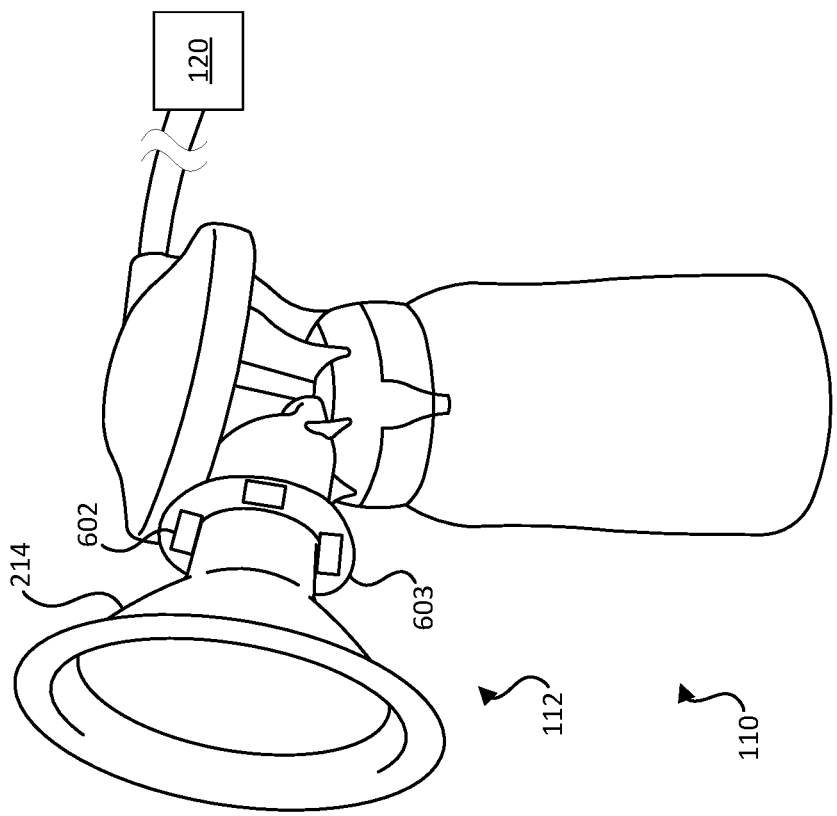
FIG. 6 illustrates an example milk collection apparatus having one or more sensors attached proximate the breast shield FIG. 7 demonstrates an example valve having a sensor.

FIG. 6 illustrates an example milk collection apparatus 110 having one or more sensors 112 attached proximate the breast shield 214. In particular, the illustrated milk collection apparatus 110 includes an outer ring 603 having one or more sensors or detectors 602 disposed on or within the ring 603. The ring 603 can be disposed outside of a fluid flow path of the milk collection apparatus 110. The one or more sensors and detectors 602 can be configured to generate light, electrical fields, magnetic fields, or other signals across a fluid flow path for detection and use in detecting characteristics present in a fluid flow path. In an example, the one or more sensors 112 can include magnetic sensors, dielectric sensors, electrical field excitation sensors, photo sensors, other non-contact external sensing mechanisms, or combinations thereof. The sensors 112 can be used to sense the movement of fluid magnitude and or timescale which would help the pump system 100 determine how the system 100 is operating relative to the production of milk. The ring 603 can be detachable from the breast shield 614.

Figure 7:
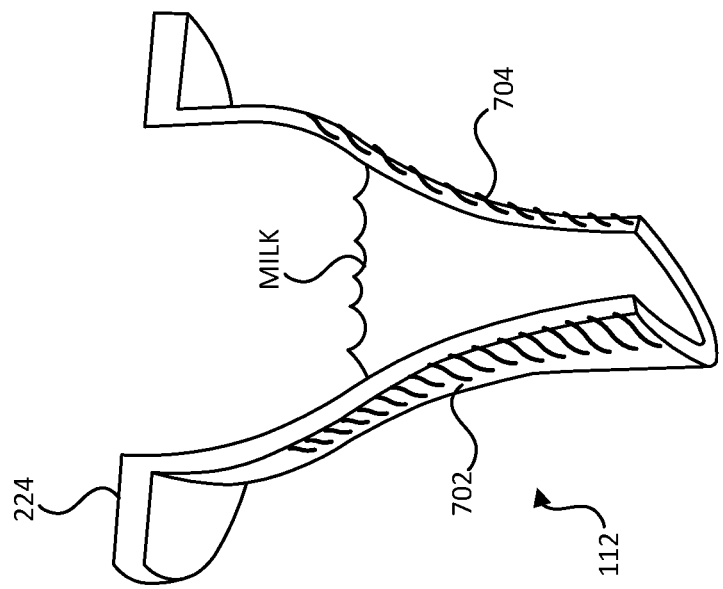

FIG. 7 demonstrates an example valve 224 having a sensor 112. As illustrated, the sensor 112 is configured as an excitation electrode 702 on one side of a flap opening of the valve 224 and a sensing electrode 704 on a second side of the flap opening. When each these flaps are actuated or moved apart, milk can be detected and measured as it moves through the valve 224. In an example, the sensor 112 is configured to measure an amount of time or extent to which the valve is open, which can be used to determine an estimate of the volume or flow rate of fluid passing through the valve 224. The sensor 112 can be configured as an impedance (resistive/capacitive/inductive) sensor. A signal from the sensor 112 can be transmitted to the pump console 120 to provide input for a software algorithm for use in determining operation of the breast pump system 100.

Figures 8A, 8B:
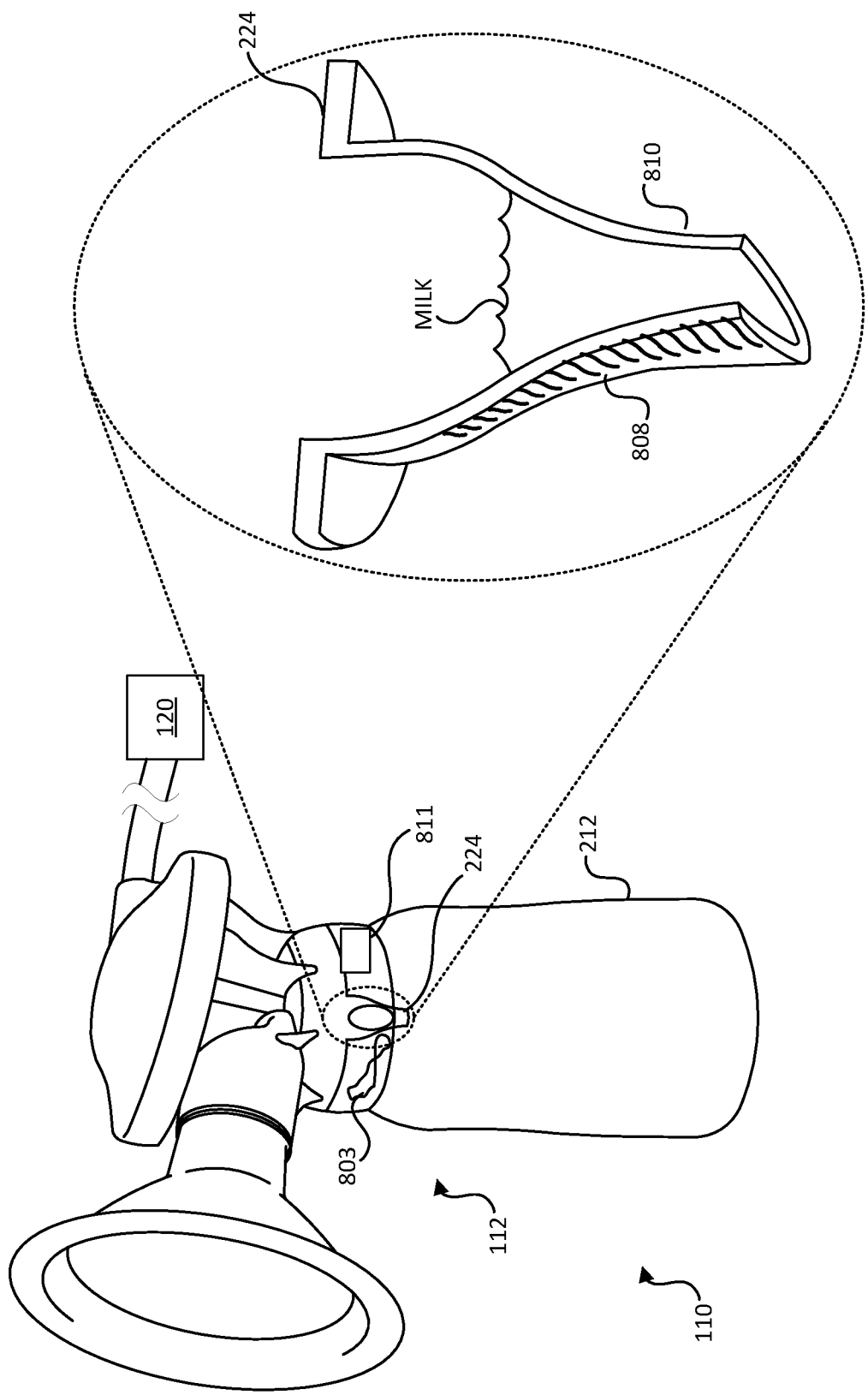
FIG. 8, which is made up of FIGS. 8A and 8B illustrates an example milk collection apparatus having a sensor configured as a magnetic sensor.

FIG. 8, which is made up of FIGS. 8A and 8B illustrate an example milk collection apparatus 110 having a sensor 112 configured as a magnetic sensor 811 disposed proximate a magnetic component 808 of the valve 224 (e.g., the valve 224 can be a duckbill valve having at least two flaps and one or more of the flaps can have a magnetic component 808). The magnetic sensor 811 can be configured to detect movement of the magnetic component 808. As the valve 224 actuates open and closed with flow of milk into the container 212, the magnetic component 808 can move, and the movement can be detected with the magnetic sensor 811 to produce data. The produced data can be transmitted to the pump console 120 via the transmitter 803. The magnetic sensor 811 can be disposed on or in a cuff or top of the container 212. The magnetic sensor 811 can be in communication with a transmitter 803 of the apparatus 110. The transmitter 803 is in wired or wireless communication with the pump console 120. The magnetic component 808 can be magnetic, ferromagnetic, or metallic component that can affect the current and or voltage in an outer sensor ring such that as the valve 224 is manipulated to open or close, the sensor 811 can provide a signal that (along with a timestamp) can be used to approximate the amount or magnitude of fluid or fluid pulses that enter the container 212.

FIG. 9, which is made up of FIGS. 9A and 9B, demonstrates an example milk collection apparatus 110 having a sensor 112 configured as a light detector 906. The valve 224 has transparent or semi-transparent sides 902. The apparatus 110 includes a light source 904 configured to transmit a wavelength of energy or light through the valve 224 to the light detector 906. The extent to which the transmitted wavelength of energy is affected as it passes from the light source 904 through the valve 224 to the detector can be used to infer the presence of a milk in the valve as well as the amount of milk therein. One or both of the light source 904 and light detector 906 can be disposed proximate the valve 224 via a ring 908. The ring 908 can be or attach to a cuff or top of the container 212. The ring 908 can further include a transmitter 910. The transmitter 910 can be in wired or wireless communication with the pump console 120. The data generated by the light detector 906 can be provided to the transmitter 910 for sending the data to the processor 124 via a wired or wireless connection for processing. Depending on the power and wavelength emitted by the light source 904 and detected by the light detector 906, the molecular composition, fat content, protein content, carbohydrate content, water content, nutritional content, other content, or combinations thereof of the milk in the valve 224 can be determined and recorded in real time as the milk passes through the valve 224. This data can help inform the pump console 120, for example, if the milk is from the front of the breast (e.g., foremilk) or the back of the breast (e.g., hindmilk) with a varied fat and other nutrient content shift over time. In addition or instead, the data can relate to movement of the valve 224, which can be used to infer an amount of fluid passing through the valve.

Figure 10:
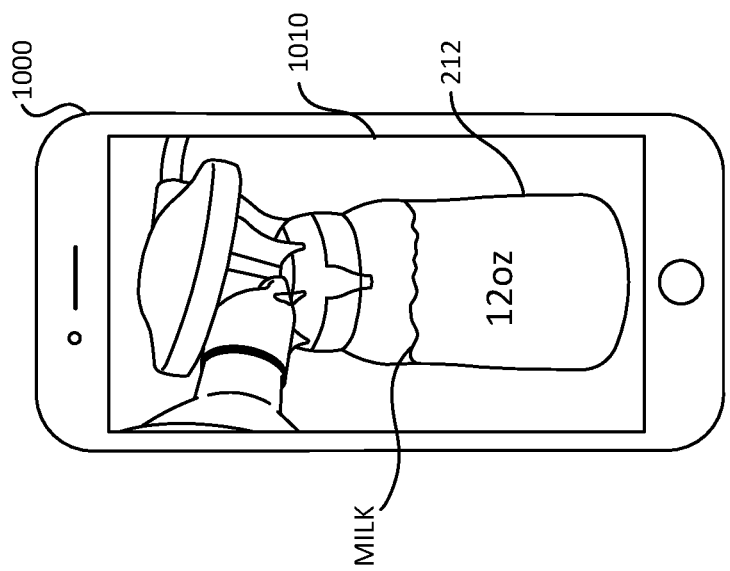
FIG. 10 illustrates the use of a mobile device with a camera as a sensor to capture an image of the container or another component of the milk collection apparatus.

FIG. 10 illustrates the use of a mobile device 1000 with a camera as a sensor 112 to capture an image 1010 of the container 212 or another component of the milk collection apparatus 110. Video or image data obtained from the camera can be analyzed to determine the fullness of the container 212. The data can also be used to determine a rate at which the container 212 is filling with milk. In an example, the image 1010 can be analyzed using a machine-vision algorithm. In an example, the container 212 can include volume markings and a machine-vision algorithm can be configured determine a volume marking most proximate to the milk level in the container 212 to determine the amount of milk in the container. In an example, the machine-vision algorithm is programmed using the OPENCV library or another machine vision library. In addition or instead, the visual qualities of the milk can be analyzed to determine properties of the milk (e.g., whether the milk is foremilk or hindmilk).

Figure 11:
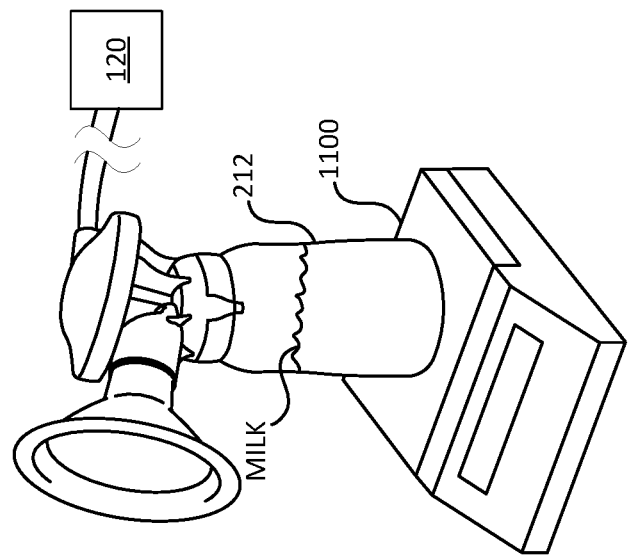
FIG. 11 illustrates the use of a weight sensor as a sensor to determine an amount of milk in the container.

FIG. 11 illustrates the use of a weight sensor 1100 as a sensor 112 to determine an amount of milk in the container 212. For example, the container 212 can be placed on a scale or other weight sensor 1100. The reading from the scale can automatically or manually be provided to the one or more processors 124 for modifying the pumping parameters.

Figure 12:
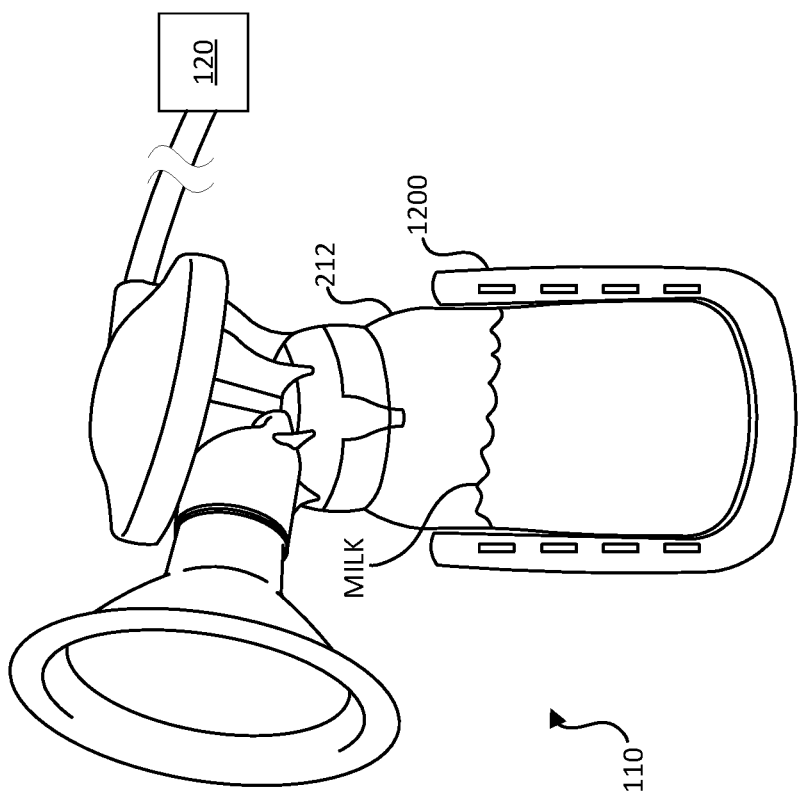
FIG. 12 illustrates an example milk collection apparatus having a sleeve having one or more sensors disposed thereon or therein to determine an amount of milk in the container.

FIG. 12 illustrates a milk collection apparatus 110 having a sleeve 1200 having one or more sensors 112 disposed thereon or therein to determine an amount of milk in the container 212. The sensors 112 can include one or more sensors as described herein, such as one or more electrical, magnetic, impedance, and or other sensors to determine the level of fluid in the collection container. The sleeve 1200 is sized and shaped to couple with or fit around the container 212. In some examples, the sleeve 1200 can be built into the container 212. Alternatively, the sleeve 1200 can be discrete from the container.

Figure 13:
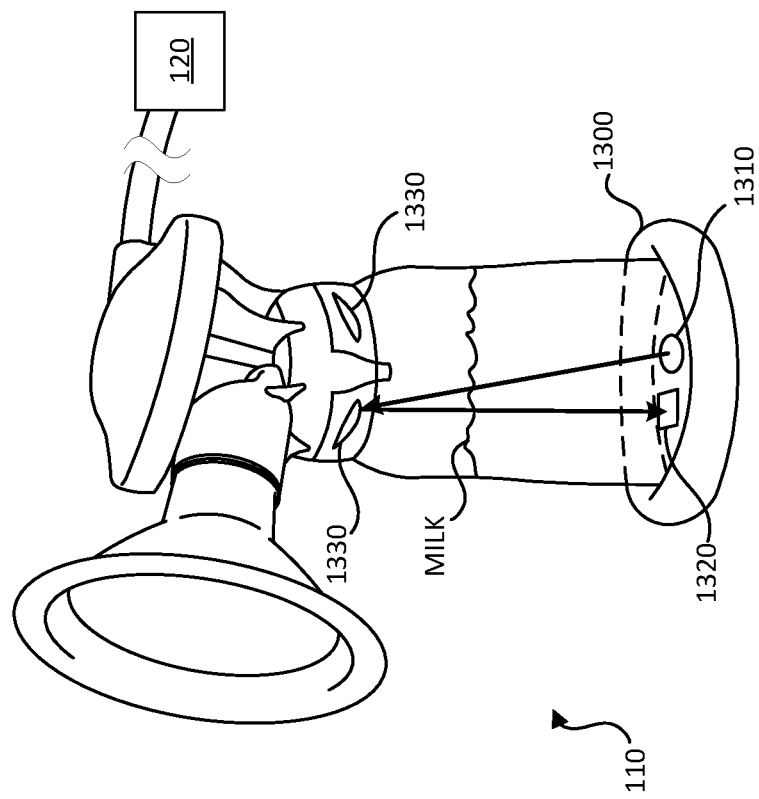
FIG. 13 illustrates an example milk collection apparatus having a holder for a container.

FIG. 13 illustrates a milk collection apparatus 110 having a holder 1300 for a container 212. The holder 1300 includes one or more light sources 1310 and one or more light sensors 1320. The light produced by the light sources 1310 can be transmitted through the container 212, reflected off of one or more reflectors 1330 and returns to be detected by the one or more light sensors 1320. The light is modified as it passes through the container 212 and any material contained therein. The properties of the received light can be analyzed to determine properties of the milk in the container 212. The reflectors 1330 can be discrete reflector components disposed within a component of the apparatus 110. Alternatively the reflector 1330 can be a component of the apparatus 110 having natural reflectivity. Although light is described, the source 1310, the sensors 1320, and the reflectors 1330 can be configured to operate using any of a variety of wavelengths of energy and need not be limited to the visible spectrum.

Figure 14:
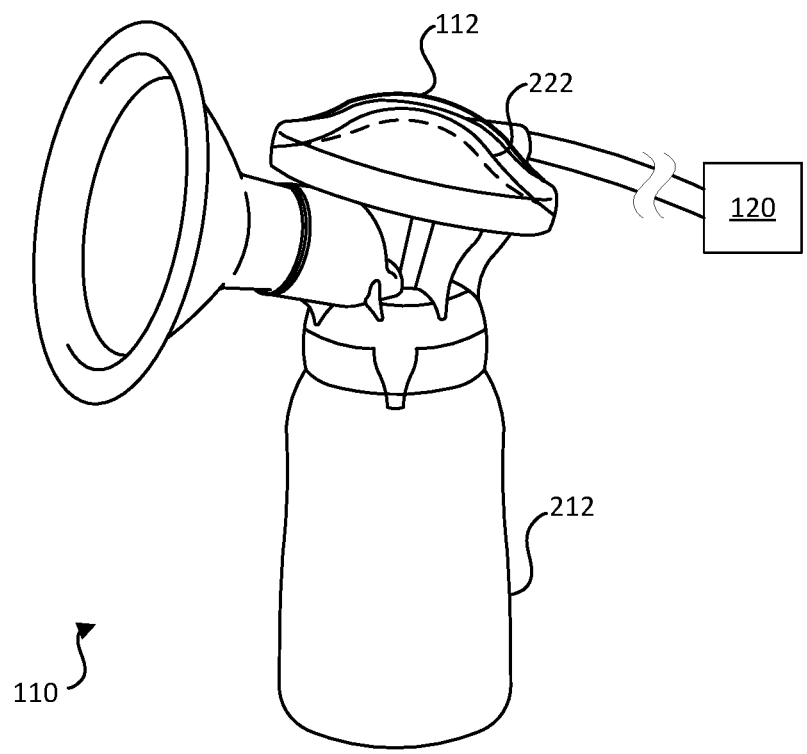
FIG. 14 illustrates an example milk collection apparatus having a sensor configured to measure deflection of the diaphragm.

FIG. 14 illustrates an example milk collection apparatus 110 having a sensor 112 configured to measure deflection of the diaphragm 222. In examples, an excitation electrode is disposed on the diaphragm 222 and a detection electrode is disposed on or within the vacuum housing 220 or vice versa. The rate and magnitude of deflection can be used to determine the pressure relationship to milk in the anterior chamber 320 of the apparatus 110 prior to the milk flowing through the valve 224 into the container 212 when a source of suction is applied. Displacement of the diaphragm 222 can be measured using, for example, capacitance as surrogate to measure expressed milk flow rate by measuring increase and decrease in capacitance as the diaphragm moves closer to the sensing electrode and farther away from it with changes in pressure.

The data from one or more of the above sensors can be used to modify operation of the system 100. Further, the pump 122 or other components of the system 100 can act as sensors themselves. For example, the behavior of the pump 122 (e.g., current draw, voltage, time needed to reach a target voltage, etc.) can act as a sensor itself and the produced data can be used to infer information regarding milk expression, pressure in the system, or other events. An example pump waveform that indicates an amount of milk expressed is shown in FIG. 15.

Determining Milk Expression Using Pumping Characteristics

Figure 15:
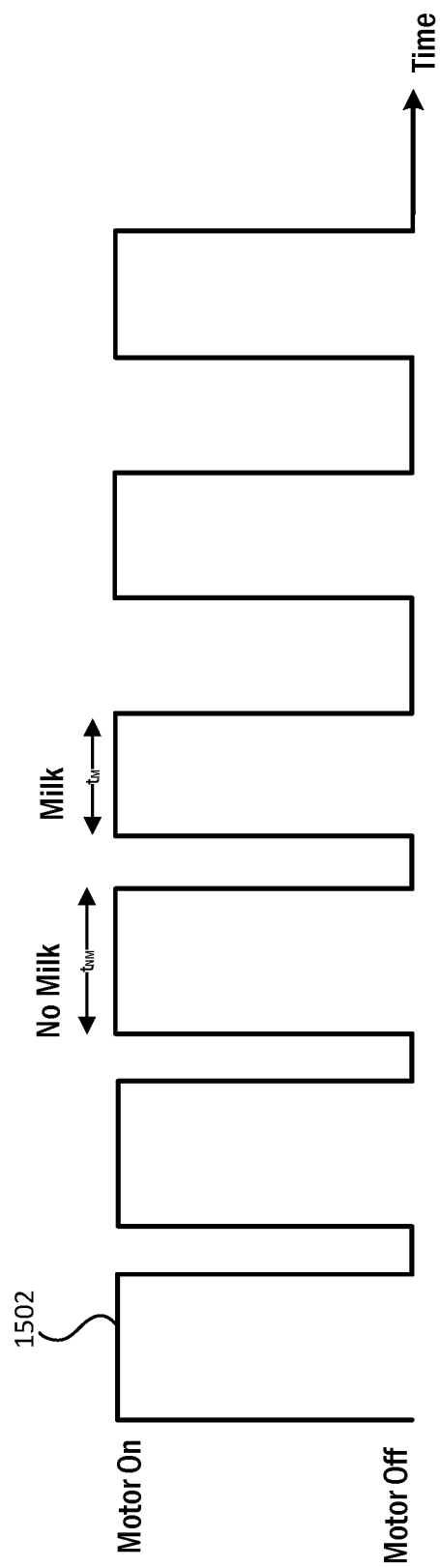
FIG. 15 illustrates a waveform that can be used to control the operation of the pump.

FIG. 15 illustrates a waveform 1502 that can be produced by the processor 124 and used to control the operation of the pump 122. The illustrated waveform 1502 a high signal corresponding to a motor on condition and a low signal corresponding to a motor off condition of a motor of the pump 122. The duty cycle of the waveform 1502 can be expressed as a percentage representing the relative amount time spent in a motor on condition compared to a motor off condition in a single cycle. The waveform 1502 can be produced by the processor 124 to control the operation of the pump 122. Although illustrated as a square waveform having binary motor on and motor off states, the waveform 1502 can take other forms, including sine, triangle, or saw tooth configurations.

The figure further illustrates how the properties of the waveform 1502 can be analyzed to determine an amount of milk in the system. For example, the processor 124 can be configured to maintain a particular vacuum pressure, such as during a hold period (see, e.g., FIG. 16). If there is expressed milk in the system (e.g., in the anterior chamber above the valve 224), the free volume is reduced, so the pump 122 does not need to work as hard to maintain the pressure. This reduction in effort can be seen in a relative amount of time spent in the motor on condition per cycle compared to the amount of time spent in the motor off condition of the cycle. As can be seen, less amount of time is needed in the motor on condition to maintain the same pressure. As such, a difference in the amount of time can allow the system to determine the volume in the anterior chamber, which can correlate to an amount of milk being present. In alternative examples, the relative amount of time spent in a motor on condition can be used across variable pressure examples as well, such that the time, power, vacuum are measured and accounted for.

In addition or instead of the relative amount of time being used, the amount of current consumed by the pump 122 or other pump 122 usage characteristics can be used as a measure to determine various parameters, such as a milk flow rate, a volume of milk expressed, or a pressure within the system. The pump can be driven in a closed-feedback to maintain constant voltage across the pump, while measuring the amount of current consumed by the pump. If there is expressed milk in the valve system, the amount of current consumed will at least temporarily decrease due milk occupying space in the anterior chamber volume making the pump 122 need to draw less current to cause a particular pressure change in the anterior chamber. Thus the changes in the current draw of the pump 122 can be tracked and used to determine an amount of milk expressed (e.g., by allowing the system to determine an amount of milk in the anterior chamber of each cycle).

Another technique can include the use of a feedback loop to drive the motor of the pump 122 at a constant voltage while measuring the current consumed by the motor. As milk accumulates in the anterior chamber, the motor does not need to work as hard to maintain the pressure, so the current consumed during the waveform can be used as a surrogate measure of the amount of milk accumulated in the duckbill valve. This power or current measurement can be used as stand-alone measure or as an additional factor for the algorithm to increase the accuracy of prediction for the milk flow rate and or the total accumulated volume.

Waveforms

Figure 16:
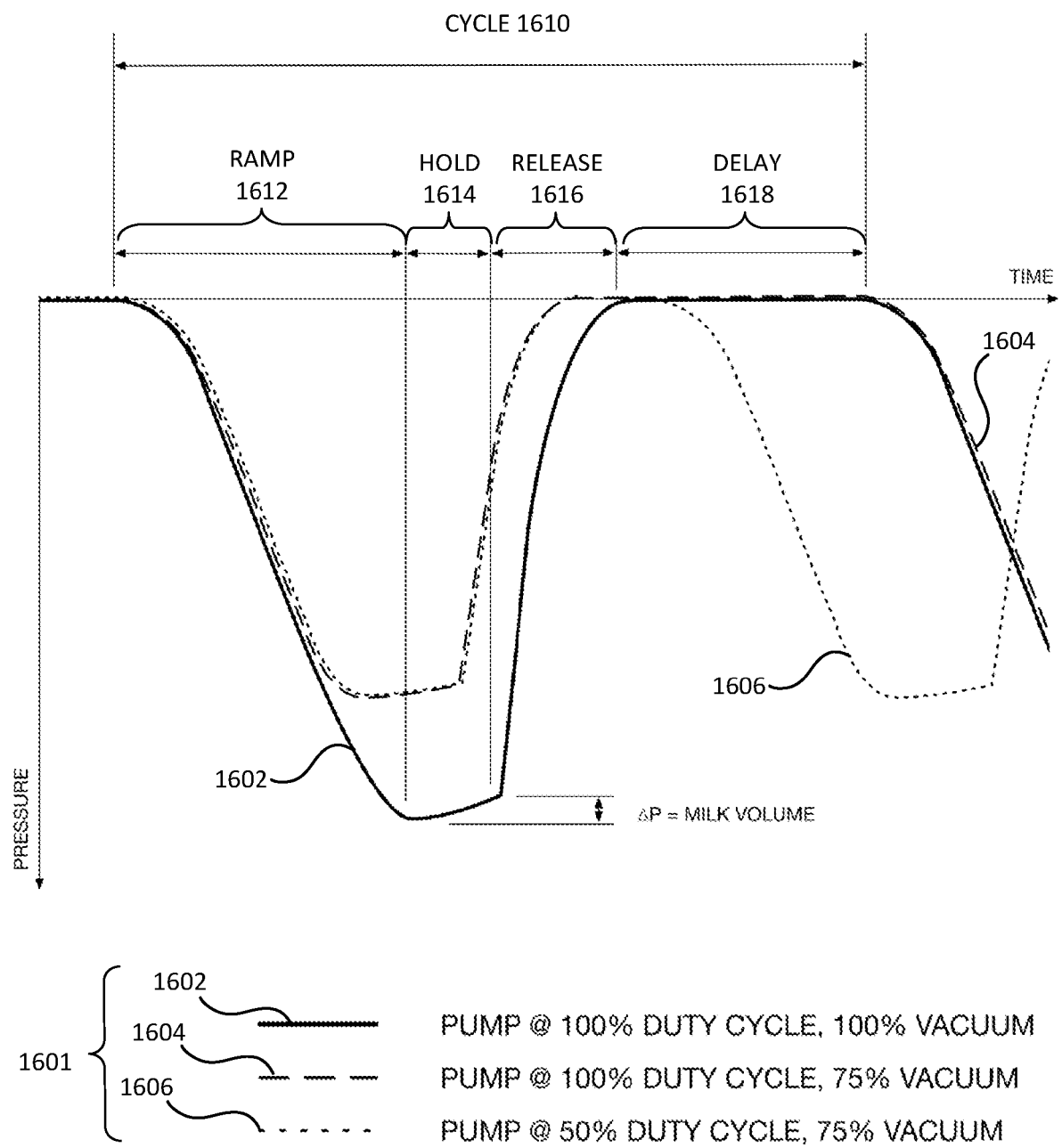
FIG. 16 illustrates example breast pump waveforms.

FIG. 16 illustrates example breast pump waveforms represented over a multitude of vacuum waveforms 1601. The waveforms 1601 are shown in terms of pressure over time. A first waveform 1602 is represented in a solid line and relates to a pump having a 100% duty cycle and 100% vacuum. A second waveform 1604 is represented with a long-dash line and relates to a pump having a 100% duty cycle and 75% vacuum. A third waveform 1606 is represented with a short-dash line and relates to a pump having a 50% duty cycle and 75% vacuum. The pressure is relative pressure within a portion of the breast pump system compared to a pressure of the environment outside of the breast pump system. The figure further shows a change in the waveforms 1601 over a cycle 1610. The cycle 1610 can be a discrete sequence of pump activity, such as can be controlled by the processor 124 via the production of a waveform, such as the one shown in FIG. 15. The illustrated cycle 1610 includes different periods, including a ramp period 1612, a hold period 1614, a release period 1616, and a delay period 1618.

The ramp period 1612 is a period of decreasing pressure, such as caused by activating the vacuum pump 122. During the ramp period 1612, the processor 124 can send a control signal to the pump 122 to cause the pump to activate in such a way as to decrease pressure in a portion of the system. In examples, the ramp period 1612 can be a fixed period of time or the ramp period 1612 can depend on an amount of time that the system takes to reach a particular pressure. A release valve (e.g., as controlled by the solenoid 126) can remain closed during the ramp period 1612 to help maintain the relatively low pressure. The length of the ramp period 1612 can relate to a relative vacuum level provided by the system, with a long ramp period 1612 resulting in lower pressure than a relatively shorter ramp period 1612. Thus, the ramp period 1612 can depend on a vacuum level setting. For example, as shown, the first waveform 1602 has a 100% vacuum (e.g., a maximum vacuum setting) level and a relatively longer ramp period 1612 compared to the second waveform 1604 and the third waveform 1606, which both have a vacuum level of 75%. The ramp period 1612 of the pump can affect the perceived comfort and perceived suction to the user. A very fast ramp period 1612 can give the user the perception of a strong suction, even though the end pressure may be the same as a relatively longer ramp period 1612. A slow ramp period 1612 can result in more comfort to the user.

The delay period 1618 is a period following the ramp period 1612 and prior to the release period 1616, during which the pressure remains relatively low. The delay period 1618 can be a period of time during which the pump 122 is inactive or during which the pump 122 operates at a reduced rate compared to the ramp period 1612. A release valve (e.g., as controlled by the solenoid 126) can remain closed during the ramp period 1612 to help maintain the relatively low pressure. As shown in FIG. 16, an amount of milk expressed during the hold period 1614 can cause a measurable change in pressure from the beginning of the hold period 1614 to the end of the hold period 1614. For example, the pressure in the anterior chamber of the milk collection apparatus can change from nominal pressure to a higher pressure as a result of milk flowing into the chamber due to a reduction in the free air volume in the chamber. This change in pressure can be detected and used to infer an amount of milk expressed. In examples, the hold period 1614 can be fixed or independently controllable (e.g., the hold period 1614 need not vary based on vacuum level or duty cycle).

The ramp period 1612 and particularly the hold period 1614 are time periods during which a highest amount of milk is expected to be expressed. Thus modifying the length of the ramp period 1612 (which can affect a vacuum level used to express milk) and the length of the hold period 1614 can affect an amount of milk produced. While a low pressure can cause more milk to be expressed, it can also cause discomfort for the mother.

The release period 1616 is a period following the hold period 1614 during which a vacuum in the system is allowed to be released such that the pressure increases relative to the pressure during the hold period 1614. During the release period 1616, the pump 122 can be off and the processor 124 can send a signal to the solenoid 126 to cause a release valve to be opened. In examples, the release period 1616 can be fixed or independently controllable (e.g., the release period 1616 need not vary based on vacuum level or duty cycle).

The delay period 1618 can be a period after the release period 1616 and prior to the end of the cycle 1610. During the delay period 1618 the pump 122 can be off and the solenoid 126 can cause the release valve to be closed or open.

Between cycles 1610 or during cycles 1610 (e.g., during the delay period 1618), the processor 124 can analyzed data collected regarding milk production during the periods and modify one or more parameters to optimize milk production and comfort of the mother during future cycles. The changes can include, for example increasing the length of one or more of the periods. Relatively shorter cycles can be selected for letdown stimulation and relatively longer cycles can be selected for expression of milk. For example, while the measured amount of milk is relatively low (e.g., has not yet satisfied a threshold), the processor 124 can control the pump 122 to provide letdown stimulation and milk production satisfies a threshold, the processor 124 can modify pumping parameters to provide expression stimulation. As described elsewhere herein, various features or characteristics can be imparted into waveforms by the pump 122 as the processor 124 detects and adapts to user preferences from input signals on other measurement devices.

Figure 17:
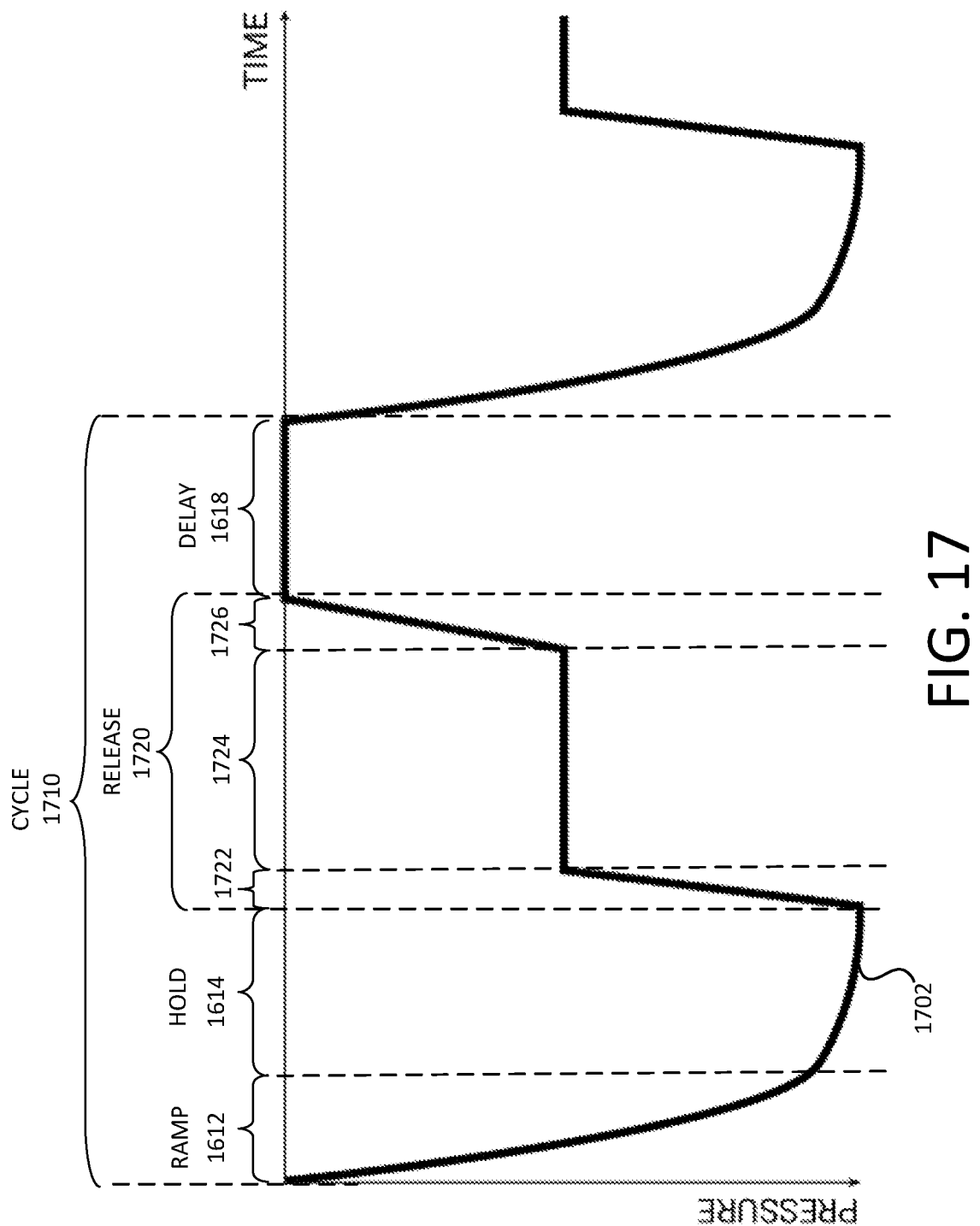
FIG. 17 illustrates an example waveform.

FIG. 17 illustrates an example waveform 1702. Like waveform 1602, the waveform 1702 includes a vacuum ramp period 1612, a hold period 1614, and a delay period 1618. Unlike the release period 1616 of the waveform 1602, the waveform 1702 includes a release period 1720 having a first release period 1722, a minor partial vacuum plateau period 1724, and a second release period 1726. The first and second release periods 1722, 1726 can have properties similar to the release period 1616. The minor partial vacuum plateau period 1724 can be a time period during which the pressure does not substantially increase. For example, while a release valve can be open during the first release period 1722, the release valve can be closed at the start of the plateau period 1724. The plateau period 1724 can be imparted into the waveform 1702 by an adaptive process (e.g., a software algorithm) of the pump console that adjusts the waveform 1702 in accordance with sensor feedback from the pump 122 to extract milk. The waveform 1702 can be cycled again or followed by other kinds of waveforms.

Figure 18:
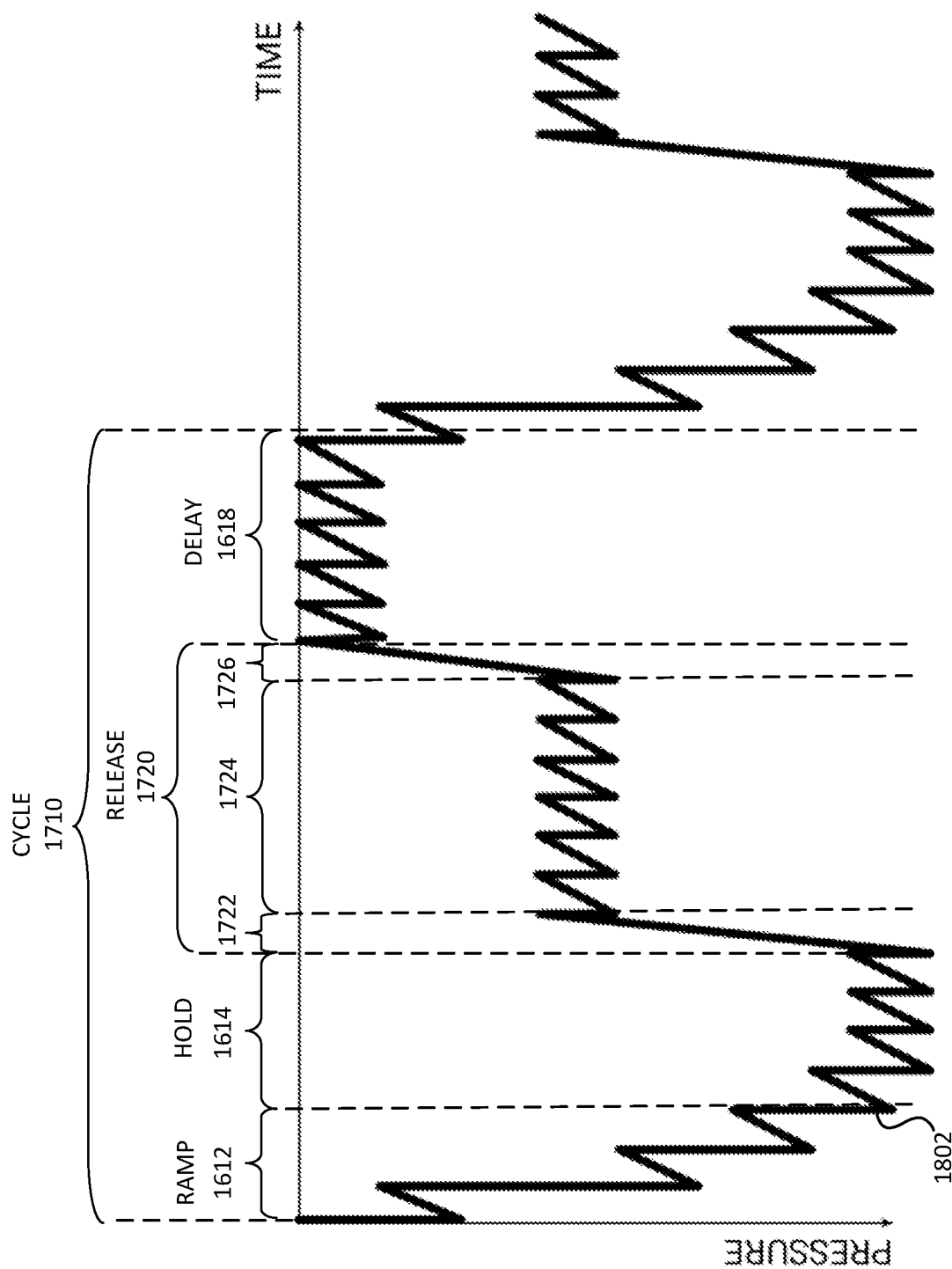
FIG. 18 illustrates an example breast pump vacuum waveform with vibrational patterns added.

FIG. 18 illustrates an example breast pump vacuum waveform 1802 with vibrational patterns added. As with FIG. 17, this waveform 1802 includes a cycle 1710 having a vacuum ramp period 1612, a first hold period 1614, a first release 1722, a minor partial vacuum plateau period 1724, a second release period 1726, and a delay period 1618. The vibrational pattern can be added by, for example, the processor 124 causing the solenoid 126 to repeatedly open and close the release valve. While the release valve, the pump 122 can be deactivated to conserve energy. And as illustrated, during the hold period 1614, plateau period 1724, and delay period 1618, while the pump 122 may typically be disabled, the pump 122 can be activated to return pressure to a relatively steady state.

Additional example waveforms that can be used are described in U.S. 62/727,909, which is tilted "Vibratory Waveform for Breast Pump", and which is hereby incorporated by reference herein in its entirety for any and all purposes. The configuration of the waveforms and the cycles provided by the system 100 can be configured to match particular milk expression patterns of the users. Example milk expression patterns are described in more detail in FIG. 19.

Milk Expression Patterns

Figure 19:
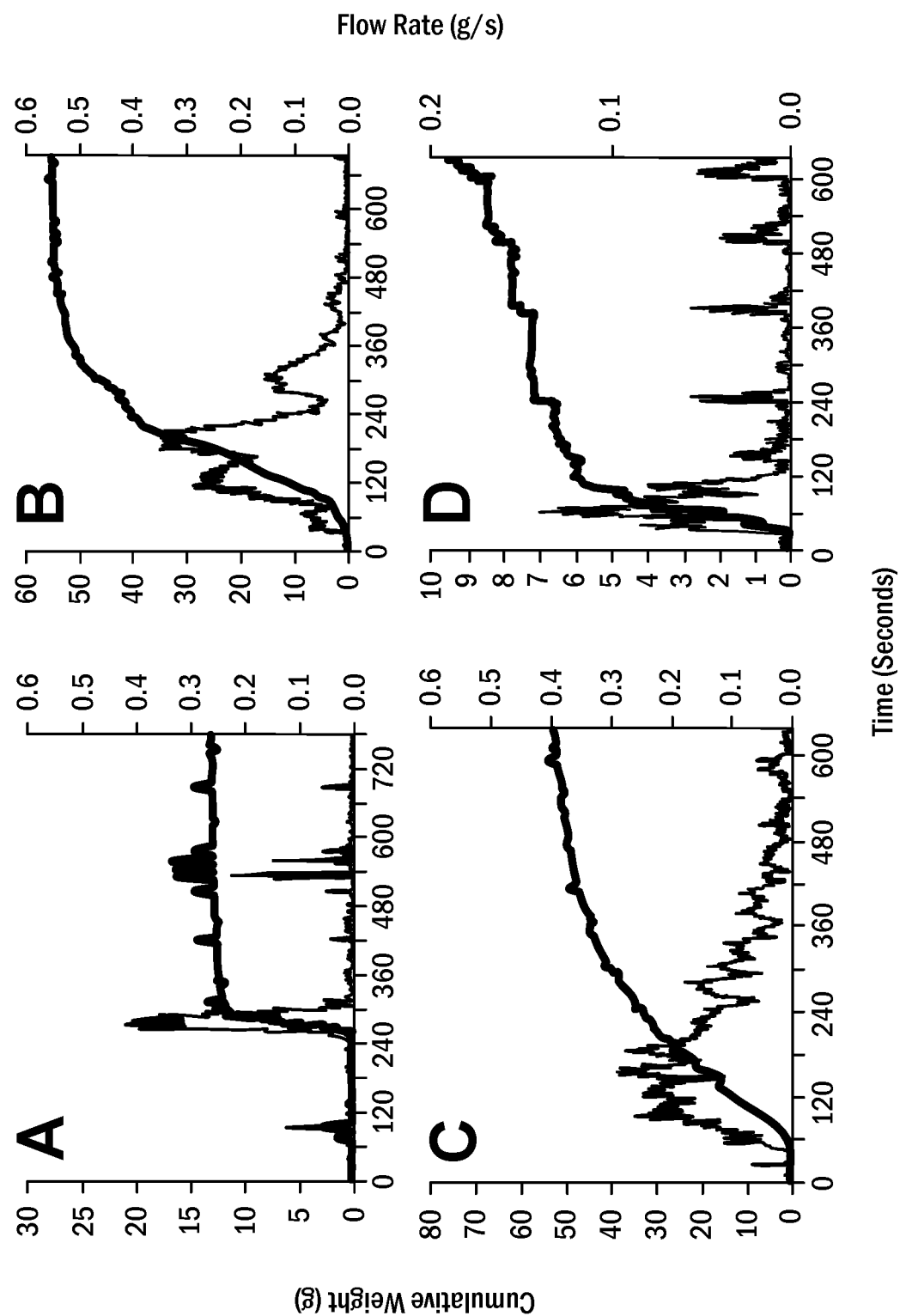
FIG. 19 illustrates four example categories of milk expression patterns.

FIG. 19 illustrates four example categories of milk expression patterns. Different users can express milk in different patterns. The technology described herein can be used to identify to which category the mom belongs and optimize the pumping waveform based thereon. For example, the system can switch between stimulation and expression mode to reduce the total breast pumping time.

As illustrated, a category A user can typically experience a first and only letdown after approximately 240 seconds of pumping. Then the user will empty most of her breast within the next 60 seconds. So to optimize pumping for this kind of user, the system can operate in a stimulation mode for approximately 240 seconds (or until milk expression is detected). Then the system can switch to an expression mode. Once the amount of milk expressed drops below a threshold amount, then the pump can indicate pumping is complete.

A category B user can typically experience a small letdown within the first sixty seconds, and then have another letdown every approximately two minutes thereafter, with the user's breast being fully empty within approximately six minutes. To optimize pumping for this user, the system 100 can operate in a stimulation mode for approximately sixty seconds (or until milk expression is detected) and then operate in an expression mode until the amount of milk expressed drops below a threshold amount. Then the system can switch back to the stimulation mode and repeat the process for a certain amount of time (e.g., six minutes) or until the amount of milk expressed while operating in an expression mode drops below a threshold.

A category C user tends to have a relatively continuous letdown and can require approximately ten minutes to empty her breast. Thus, the system can optimize pumping for this user by providing a stimulation mode, switching to an expression mode once milk expression is detected and continue to operate in the expression mode until the milk expression drops below a threshold.

A category D user can have a relatively large letdown within the first minute and have small letdowns every subsequent two minutes and will require approximately ten minutes to empty most of her breast. To optimize for a category D user, the system can start in stimulation mode for the first minute and switch to expression once the pump detects milk expression. Once the amount of milk expressed drops below a threshold, the pump can will switch back to stimulation mode. This process can be repeated for 5 times to ensure that breast milk is emptied from the breast.

The system can detect to which category the user belongs based on analyzing a cumulative amount of weight or flow rate of the user over time and comparing the results to known categories (e.g., by fitting a curve corresponding to a category to the flow rate and/or weight). In other examples, the system can receive input from the user indicating to which category the user belongs. The system can then store category information and operate according to the user's category.

Figure 20:
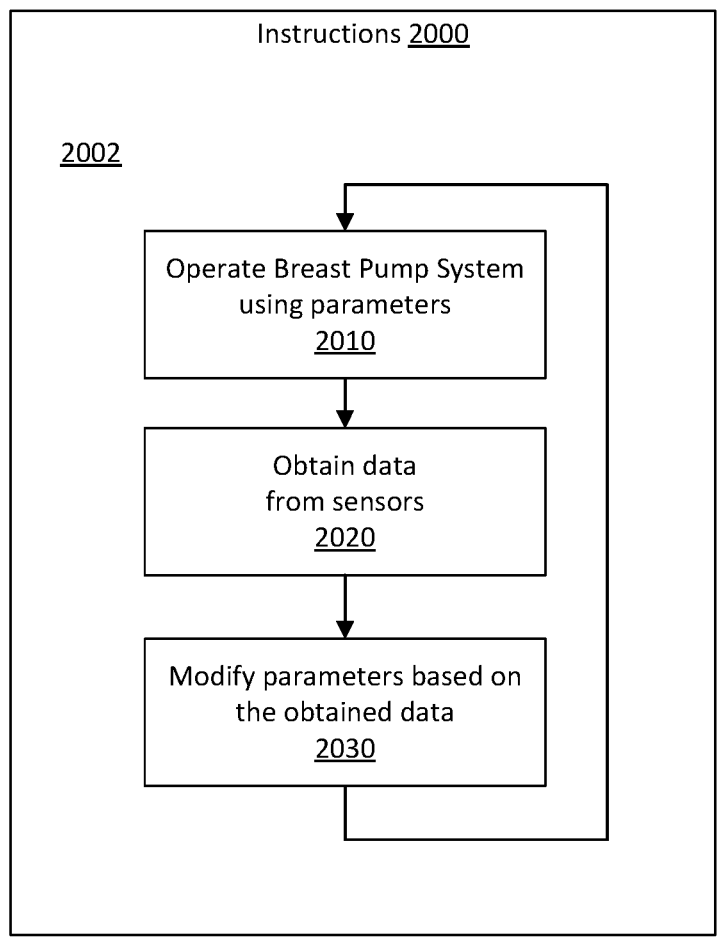
FIG. 20 illustrates example instructions implementing a process.

An overall example process for operating the breast pump system 100 is described in FIG. 20.

Example Process

FIG. 20 illustrates example instructions 2000 implementing a process 2002. Although shown as being implemented with instructions 2000, the operations of the process 2002 can be performed using one or more circuits configured to perform operations without needing instructions 2000 to be executed. The process 2002 can begin with operation 2010. In some examples, the process 2002 can begin responsive to the pump console 120 being powered on or the system detecting that a user pressed a start button.

Operation 2010 includes operating the breast pump system 100 using parameters. The parameters include the parameters described herein and can correspond to values stored by the pump console 120 and used by the processor 124 to control operation of the pump system 10.

In an example, the two primary components used to operate the breast pump system are the pump 122, which creates a vacuum within the system and the solenoid 126, which releases the vacuum. Both the pump 122 and the solenoid 126 can be controlled via signals from the processor 124. The processor 124 can generate such signals based on a wide variety of parameters.

The parameters that can be changed include length of the cycle 1710, length of the ramp period 1612, length of the hold period 1614, length of the release period 1616, length of the delay period 1618, maximum pressure level, maximum vacuum level, minimum pressure level, minimum vacuum level, vibration patterns, presence of plateaus during the cycle 1600 (see, e.g., FIG. 17), slope of pressure changes over time during the ramp period 1612 or release period 1616, other features or combinations thereof.

Parameters can exist at relatively high and relatively low levels, with some parameters controlling the values of other parameters. For example, the pump can have a parameter that specifies a particular phase of pumping in which the breast pump system 100 is operating. For instance, the breast pump system 100 selectively operate in a stimulation phase or an expression phase. The stimulation phase can be a phase configured to stimulate a breast to produce milk and the expression phase can be a phase configured to facilitate the extraction of milk once milk begins to be expressed in the stimulation phase. The phase in which the breast pump system 100 operates can affect other parameters. For example, a stimulation phase can have relatively shorter waveform cycles and the expression phase can have relatively longer waveform cycles as specified by one or more different parameters associated with each type of phase. Following operation 2010, the flow of the process 2002 can move to operation 2020.

Operation 2020 includes obtaining data from one or more sensors. This operation 2020 can include the processor 124 receiving data from one or more sensors 112 of the milk collection apparatus 110, one or more sensors of 128 the pump console 120, other sensors, or combinations thereof. The data can include measurements directly or indirectly obtained by the one or more sensors regarding the milk collection apparatus. For example, a sensor 128 within the pump console 120 can be used to measure a power draw of the one or more pumps 122, which can be used to measure an amount of milk in the milk collection apparatus 110. In this example, while the sensor 128 directly measures power draw of the one or more pumps 122, the obtained measurements themselves can be used by the processor 124 to measure an amount of milk in the anterior chamber 320 of the milk collection apparatus 110. Thus, the sensor 128 can be considered to directly measure power draw and indirectly measure the amount of milk because the amount of milk is correlated to the power draw. In some examples, this operation 2020 includes receiving data pushed from the sensors, in other examples, this operation 2020 can include sending requests for data from the sensors. The operation 2020 can include determining characteristics of expressed milk, such as milk flow rate or volume. The operation 2020 can include causing the sensors to obtain data. Following operation 2020, the flow of the process 2002 can move to operation 2030.

Operation 2030 includes modifying the parameters based on the obtained data. The operation 2030 can include modifying the parameters directly based on the obtained data, or the operation 2030 can include processing (e.g., analyzing) the obtained data and using the processor 124 and modifying the parameters based on the processing.

In an example, the processing includes comparing at least some of the data with a threshold and, responsive to the threshold being satisfied, modifying one or more parameters. In many examples, the modifying is performed based on whether and to what extend the obtained data indicates the production of milk. This can include data indicating a volume of milk collected or a rate at which milk is being collected. As described above, the modifying of the parameters can be configured to stimulating a breast to express milk, obtain milk from the breast once milk is expressed, and then stop pumping once a sufficient amount of milk has been expressed. The modifying can be based on real-time data obtained from the sensors. The modifying can be further based on comparisons of current data with previous data stored in the system (e.g., stored in the memory 132).

The processing can be based on, for example, statistical analysis. In some examples, the processing is based on changes in data over time, such as a rate of change in pressure, current draw, estimated flow rate, or other data obtained by or inferred from the sensors. In some examples, the processing can be performed with a machine learning algorithm trained to produce output based on data provided as input. For example, any of a variety of machine-learning or artificial intelligence algorithms can be used, such as simulated annealing or genetic algorithms. To use those algorithms, each of the various parameters are randomly adjusted simultaneously in each cycle, and the unique parameters to each individual person that influence the rate of expression are found. For example, the algorithms can be trained in real time on how the change in parameters affect the volume of milk produced. Over time, the algorithms become customized to the particular user.

In an example, a genetic algorithm can be used. Tuning of parameters using a genetic algorithm can occurs over one or more sessions. In an example implementation, various parameters are initially randomly chosen and constitute the search space (which can be constrained by comfort and safety) defined as Session S1. A parameter from the search space for S1 can be chosen for each cycle or for n-amount of cycles, and the flow rate is measured. For the next Session S2, the top-n parameters that result in the highest flow rates are selected for breeding the next generation of parameters for Session S2. For the n settings, the system can randomly generate nC2 pairs between the parameters. For each pair (e.g., corresponding to a father and mother), i children will be randomly generated with each child will having half of its parameters from the father and half from the mother. Which parameters from the mother and the father that gets passed down to the children can be at least pseudorandom. These children constitute the search space for Session S2. At the completion of Session S2, the top-n parameters that resulted in the highest flow rate for this session can be selected for breeding the next generation of parameters for Session S3. As such, the system can learn from the user over multiple sessions. The search space and performance for each setting can be stored in memory the device or at an external location (e.g., a removable memory device, a mobile device, at a server, or another location) and can be unique to each user. The system can also generate an aggregate model from many users, to create a model that can work decently well for a subset of users. For example, one hundred users can use different pumps simultaneously, and the system can leverage the parallel users to iterate through the search space much faster to generate a generalizable model. This allows the system to search in a larger search space, which can allow for not only rise time, pressure, hold time, delay, but also unique waveforms as well. Models can be shared between pumps to generate a generalizable model via a network (e.g., the Internet, via BLUETOOTH, or another communication medium).

Following operation 2030, the flow of the process 2002 can return to operation 2010.

Although this detailed description has set forth certain embodiments and examples, the present disclosure extends beyond the specifically disclosed embodiments to other alternative embodiments and/or uses of the embodiments and modifications and equivalents thereof. Thus, it is intended that the scope of the present disclosure should not be limited by the particular disclosed embodiments described above.

What is claimed is:

1. A breast pump system, comprising:
a milk collection apparatus comprising a pump volume;
a pump console comprising one or more processors and a pump, wherein the pump is configured to induce suction at the milk collection apparatus based on one or more pumping parameters; and
a pressure sensor configured to measure negative pressure within the pump volume,
wherein the one or more processors are configured to:
control the pump through one or more milk expression cycles, wherein each of the one or more milk expression cycles includes at least one period;
detect, using the pressure sensor, a change from a first negative pressure measured during the at least one period of a first milk expression cycle of the one or more milk expression cycles to a second negative pressure measured during the at least one period of a second milk expression cycle of the one or more milk expression cycles;
determine an estimated volume of milk within the milk collection apparatus, based on the detected change in negative pressure; and
modify at least one of the one or more pumping parameters, based at least in part on the detected change in negative pressure and the estimated volume of milk.

2. The breast pump system of claim 1, wherein the milk collection apparatus further comprises a breast shield, and wherein the pressure sensor is directly attached to the breast shield.

3. The breast pump system of claim 1, wherein the pump console further comprises a current sensor, wherein the current sensor is configured to measure current draw of the pump, and wherein the one or more processors are configured to determine the estimated volume of milk within the milk collection apparatus, further based on the current draw.

4. The breast pump system of claim 1, wherein the one or more pumping parameters are selected from the group consisting of a ramp time, a hold time, a duty cycle, a release time, and a pumping waveform.

5. The breast pump system of claim 1, wherein the one or more processors are further configured to:
determine a milk ejection pattern for a user of the breast pump system based on a volume of milk expressed; and
modify at least one of the one or more pumping parameters based on the determined milk ejection pattern.

6. The breast pump system of claim 5, wherein modifying the at least one of the one or more pumping parameters based on the determined milk ejection pattern comprises modifying a stimulation parameter.

7. The breast pump system of claim 5, wherein determining the milk ejection pattern comprises determining a flow rate of the volume of milk expressed over time.

8. The breast pump system of claim 1, wherein the at least one period for each of the one or more milk expression cycles comprises a ramp period, a hold period, and a release period.

9. The breast pump system of claim 1, wherein the at least one period comprises a hold period.

10. A breast pump system comprising:
a milk collection apparatus;
a pump;
a current sensor configured to measure a current draw of the pump;
a voltage sensor configured to measure a voltage draw of the pump; and
one or more processors configured to:
control the pump to induce suction at the milk collection apparatus based on one or more pumping parameters;
determine an estimated volume of milk accumulated within the milk collection apparatus based on the current draw and the voltage draw; and
modify at least one of the one or more pumping parameters based on the estimated volume of milk.

11. The breast pump system of claim 10, wherein the one or more processors are further configured to determine a reduction in an amount of effort expended by the pump, and wherein determining the estimated volume of milk accumulated within the milk collection apparatus is determined based on the reduction in the amount of effort, thereby being based on the current draw.

12. The breast pump system of claim 10, further comprising a pump console comprising the pump, the current sensor, and the one or more processors.

13. A breast pump system comprising:
a milk collection apparatus comprising a pump volume;
a pump;
a pressure sensor configured to measure a negative pressure within the pump volume;
a current sensor configured to measure a current draw of the pump;
a voltage sensor configured to measure a voltage draw of the pump; and
one or more processors configured to:
control the pump to induce suction at the milk collection apparatus over a cycle based on one or more pumping parameters;
determine an estimated volume of milk accumulated within the milk collection apparatus based on the current draw, the voltage draw and on a change in the negative pressure measured using the pressure sensor; and
modify at least one of the one or more pumping parameters based on the estimated volume of milk.

14. The breast pump system of claim 13, further comprising a pump console including the pump, the pressure sensor, and the current sensor.

15. The breast pump system of claim 13, wherein the change in negative pressure is selected from the group consisting of a change within the cycle and a change between the cycle and another cycle.

16. The breast pump system of claim 13, wherein the cycle is a milk expression cycle.

17. The breast pump system of claim 13, wherein modifying at least one of the one or more pumping parameters includes transitioning from stimulation pumping parameters to expression pumping parameters or transitioning from expression pumping parameters to stimulation pumping parameters.

18. A breast pump system, comprising:
a milk collection apparatus comprising a pump volume;
a pump console comprising one or more processors and a pump, wherein the pump is configured to induce suction at the milk collection apparatus based on one or more pumping parameters; and
a pressure sensor configured to measure negative pressure within the pump volume,
wherein the one or more processors are configured to:
control the pump through a milk expression cycle that includes at least one of a hold period or a release period;
detect, using the pressure sensor, a change in negative pressure measured during at least one of the hold period or the release period;
determine an estimated volume of milk within the milk collection apparatus, based on the detected change in negative pressure; and
modify at least one of the one or more pumping parameters, based at least in part on the detected change in negative pressure and the estimated volume of milk.

* * * * *